US012564393B2

(12) United States Patent
Agnihotri et al.

(10) Patent No.: US 12,564,393 B2
(45) Date of Patent: Mar. 3, 2026

(54) ACCESS SITE MANAGEMENT SYSTEM FOR PERCUTANEOUS VASCULAR ACCESS

(71) Applicant: xDot Medical Inc., Maple Grove, MN (US)

(72) Inventors: Aashiish Agnihotri, Maple Grove, MN (US); Jeffrey Sandstrom, Scandia, MN (US); Steven M. Maurer, Minneapolis, MN (US)

(73) Assignee: xDot Medical Inc., Maple Grove, MN (US)

( * ) Notice: Subject to any disclaimer, the term of this patent is extended or adjusted under 35 U.S.C. 154(b) by 267 days.

(21) Appl. No.: 18/205,147

(22) Filed: Jun. 2, 2023

(65) Prior Publication Data

US 2023/0309979 A1      Oct. 5, 2023

Related U.S. Application Data

(63) Continuation-in-part of application No. 17/811,359, filed on Jul. 8, 2022, now Pat. No. 11,998,182, which is a continuation of application No. 17/457,169, filed on Dec. 1, 2021, now Pat. No. 11,382,609.

(60) Provisional application No. 63/424,706, filed on Nov. 11, 2022, provisional application No. 63/120,795, filed on Dec. 3, 2020.

(51) Int. Cl.
*A61B 17/00* (2006.01)
*A61B 17/04* (2006.01)

(52) U.S. Cl.
CPC ...... *A61B 17/0057* (2013.01); *A61B 17/0401* (2013.01); *A61B 2017/00663* (2013.01); *A61B 2017/00867* (2013.01); *A61B 2017/0496* (2013.01)

(58) Field of Classification Search
CPC .. A61B 2017/00663; A61B 2017/0409; A61B 2017/0496
See application file for complete search history.

(56) References Cited

U.S. PATENT DOCUMENTS

| | | | |
|---|---|---|---|
| 5,496,332 A | 3/1996 | Sierra et al. |
| 5,836,955 A | 11/1998 | Buelna et al. |
| 6,464,707 B1 | 10/2002 | Bjerken |
| 10,765,418 B2 | 9/2020 | Foerster |
| 11,998,182 B2 | 6/2024 | Agnihotri |
| 2008/0097480 A1 | 4/2008 | Schorr et al. |
| 2009/0299409 A1 | 12/2009 | Coe et al. |
| 2010/0256679 A1 | 10/2010 | Ducharme |
| 2010/0262166 A1 | 10/2010 | Boraiah et al. |
| 2010/0305609 A1 | 12/2010 | Cartledge et al. |
| 2012/0010470 A1 | 1/2012 | Ducharme et al. |

(Continued)

OTHER PUBLICATIONS

International Search Report and Written Opinion mailed Aug. 23, 2023 for Application No. PCT/US2023/024275 (10 pp).

*Primary Examiner* — Alexander J Orkin
(74) *Attorney, Agent, or Firm* — Fox Rothschild LLP

(57) ABSTRACT

The disclosure provides a dynamic vascular access and closure device for radial cinching of an access site. The device includes a tensioning tube, a resilient member disposed within the tensioning tube, and a plurality of sutures extending axially between a distal end of the tensioning tube and a proximal end of the tensioning tube. A proximal end of each of the plurality of sutures can be configured to attach to the resilient member such that movement of that suture causes compression or extension of the resilient member within the tensioning tube to provide cinching to the sutures.

10 Claims, 31 Drawing Sheets

(56)                       References Cited

U.S. PATENT DOCUMENTS

| | | | |
|---|---|---|---|
| 2012/0071903 | A1 | 3/2012 | Knoell |
| 2012/0191133 | A1 | 7/2012 | Ferree |
| 2014/0354808 | A1 | 12/2014 | Hansen |
| 2015/0080902 | A1 | 3/2015 | Jaramillo et al. |
| 2017/0086807 | A1 | 3/2017 | Larzon et al. |
| 2018/0228478 | A1 | 8/2018 | Fortson |
| 2019/0336116 | A1 | 11/2019 | Walters et al. |
| 2022/0175356 | A1 | 6/2022 | Agnihotri |

1500

ACCESS SITE MANAGEMENT SYSTEM FOR PERCUTANEOUS VASCULAR ACCESS

CLAIM OF PRIORITY

This application is a continuation in part of U.S. patent application Ser. No. 17/811,359, filed on Jul. 8, 2022, which is a continuation of U.S. patent application Ser. No. 17/457, 169 (now U.S. Pat. No. 11,382,609), which claims priority to U.S. Provisional Appl. No. 63/120,795 filed on Dec. 3, 2020. This application also claims priority to U.S. Provisional Appl. No. 63/424,706 filed on Nov. 11, 2022. The disclosure of each of these priority applications is incorporated herein by reference in its entirety.

FIELD OF THE DISCLOSURE

The present disclosure generally relates devices and methods for gaining percutaneous access to the lumen of a blood vessel and for subsequently closing the access site into the blood vessel.

BACKGROUND OF THE DISCLOSURE

Minimally-invasive, catheter-based interventions have in many ways revolutionized the treatment of vascular diseases. In many interventional procedures, an interventional device is introduced to the body through the patient's artery or vein (percutaneous approach). For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the vascular system. While these procedures present various medical advantages, the potential for bleeding during the procedure can present dangers to the patient. As such, intravascular and intraluminal procedures unavoidably present the problem of stopping the bleeding at the percutaneous puncture after the procedure has been completed and after the instrument (and any insertion sheaths used therewith) has been removed.

Moreover, many such interventional processes often require multiple accesses to the blood vessel for which the percutaneous access site must remain open for long periods of time without excessive bleeding. Physicians may be required to manually prevent excessive bleeding during temporary closures, such as those occurring when changing catheters, dilators, or sheaths. Existing devices often do not provide access site management capabilities that prevent bleeding (e.g., during placement and removal of a vascular sheath) without manual intervention and/or do not facilitate multiple accesses into the vascular interior. Such devices may close an access site at the end of a procedure but require a new access site for later repeat access.

These problems are exacerbated when large bore access is required (e.g., in procedures such as transcatheter structural heart therapies (Transcatheter Aortic Valve Replacement (TAVR), Transcatheter Mitral Valve Replacement/Repair (TMVR/r) etc.), temporary mechanical circulatory support implantation (percutaneous Ventricle Assist Devices or pVADs), and percutaneous endovascular aortic abdominal aneurysm repair (PEVAR) where the size of catheters are typically in the range of 10-24 French or larger. Existing vascular closure devices are designed for small bore access, whereas many new interventional procedures require larger, more complex catheters. For this reason, some interventional procedures using larger catheters rely on a vessel cutdown to access the vein or artery. Using a surgical cutdown to access the blood vessel undermines the minimally-invasive aspect of the interventional procedure. Additionally, vessels of elderly patients are often heavily calcified, which can lead to closure difficulty and a high failure rate of conventional closure methods.

The current disclosure describes devices and methods directed towards solving some of the issues discussed above.

SUMMARY OF THE DISCLOSURE

Disclosed scenarios provide a dynamic vascular access and closure device and methods of use thereof.

For example, some of the disclosed scenarios include a dynamic vascular access and closure device for radial cinching comprising a tensioning tube that may include a resilient member disposed within the tensioning tube; and a plurality of sutures extending axially between a distal end of the tensioning tube and the proximal end of the tensioning tube. A proximal end of each of the plurality of sutures can be configured to attach to the resilient member such that movement of that suture causes compression or extension of the resilient member within the tensioning tube. The resilient member can comprise a spring.

The distal end of each of the plurality of sutures can be coupled to a vascular anchor. The vascular anchor can be a nitinol tube anchor (e.g., having three hooks) or a nitinol wire anchor.

The dynamic vascular access and closure device can further include a suture lock. In some embodiments, the sutures, vascular anchors, and suture lock can be a body-absorbable material. The vascular anchors can be nitinol anchors. In some implementations, the proximal end of each of the plurality of sutures may include a suture stop.

The dynamic vascular access and closure device can further include a resilient member stop within the tensioning tube (e.g., a step defined by a change in an internal diameter of the tensioning tube). Optionally, a force applicator may be disposed at a proximal end of the resilient member. The compression or extension of the resilient member against the resilient member stop can be the force applicator compressing the spring against the resilient member stop.

In some embodiments, at least one of the sutures can be configured to attach to a blood vessel and a distal end of the at least one suture can be configured to attach to the tensioning tube. In further embodiments, the resilient member can be configured to be in a first position to cause the plurality of sutures to cinch a vascular access site situated between the sutures when the sutures are attached to a blood vessel; or in a second position when the plurality of sutures are pulled to open the vascular access site, wherein a first length of the resilient member in the first position is greater than a second length of the resilient member in the second position.

Another scenario can include a dynamic vascular access and closure device including a plurality of sutures having a proximal end and a distal end, each of the plurality of sutures having a suture stop at the corresponding proximal end; a tensioning tube assembly comprising: a body having distal end and a proximal end, and a spring. The sutures can extend axially through the tensioning tube body and pulling of the sutures can cause application of pressure to the spring, via the suture stops. A tensioning of the plurality of sutures may be caused by opening of a vascular access site located between the plurality of sutures when the plurality of sutures are deployed to a blood vessel.

The distal end of each of the plurality of sutures may include a vascular anchor. The vascular anchor can be a nitinol tube anchor (e.g., having three hooks) or a nitinol wire anchor.

The suture stops may be knots placed in the proximal end of the sutures. The dynamic vascular access and closure device may further include a force applicator, which may be a hollow tube coaxial with the body of the tensioning tube and disposed at least partially inside the body of the tensioning tube such that a distal end of the force applicator contacts a proximal end of the spring. In some embodiments, the suture stops are disposed outside a proximal end of the force applicator. Optionally, a position of the force applicator with respect to the tensioning tube may be adjustable for increasing or decreasing pressure applied to the spring.

The dynamic vascular access and closure device may further include a suture lock. The suture lock can be disposed at the distal end of the tensioning tube and may be configured to be locked to the sutures while the sutures are under tension. The suture lock may be a ferrule configured to be crimped around the plurality of sutures. In other embodiments, the suture lock may be a semi-permanent suture lock.

Yet another scenario may include a dynamic vascular access and closure device for radial suture cinching including a plurality of vascular anchors configured for attachment to a blood vessel; a plurality of sutures having a proximal end and a distal end, the proximal ends having a suture stop and the distal ends being connected to the vascular anchors; a tensioning tube having a distal end and a proximal end, the distal end of the tensioning tube having a smaller diameter than the proximal end of the tensioning tube; and an inner biasing tube disposed at least partially inside the proximal end of the tensioning tube. The dynamic vascular access and closure device can further include a compression spring having a distal end and a proximal end, the spring being disposed inside the tensioning tube between the distal end of the tensioning tube and the inner biasing tube, wherein the distal end of the spring contacts a shoulder of the tensioning tube and the proximal end of the spring contacts the distal end of the biasing tube and a suture lock disposed between the distal end of the tensioning tube and the anchors. The sutures can extend axially through the tensioning tube, inner biasing tube, spring, and suture lock. The proximal end of the inner biasing tube can contact the suture stops. The inner biasing tube may be configured to transfer spring force from the compression spring to the plurality of sutures to cause opening or closing of a vascular access site located between the plurality of anchors when deployed on a blood vessel.

In various scenarios, methods of use of any of the dynamic vascular access and closure device can include deploying the plurality of sutures around the vascular access site (e.g., via the vascular anchors), inserting an interventional device into the vascular access site, and removing the interventional device from the vascular access site. Insertion of the interventional device into the vascular access site may cause tensioning of the plurality of sutures due to an increase in diameter of the vascular access site and compression of the compression spring. Removal of the of the interventional device can cause expansion of the compression spring and a dynamic closure of the vascular access site by cinching of the plurality of sutures.

Other scenarios include a dynamic vascular access and closure device for radial cinching including a tensioning tube including a resilient member disposed within the tensioning tube, a plurality of sutures extending axially between a distal end of the tensioning tube and a proximal end of the tensioning tube, and tension lock having a first position and a second position. A proximal end of each of the plurality of sutures may be configured to attach to the resilient member such that movement of the plurality of sutures causes compression or extension of the resilient member within the tensioning tube. In the first position, the tension lock may be configured to hold the resilient member in a compressed state, causing slack in the sutures; and in the second position, the tension lock may be configured to permit extensions of the resilient member, causing tension in the sutures. The tension lock may be a frangible bridge or a trigger suture.

The tensioning tube may further include a slot and the force applicator may further include a pin. In the first position, the pin may engage a stop on the tensioning tube. In the second position, the force applicator may be rotated such that the pin engages the slot.

Other scenarios include a dynamic vascular access and closure device including a plurality of sutures each having a proximal end and a distal end, each of the plurality of sutures having a suture stop at the corresponding proximal end, a tensioning tube including a body having distal end and a proximal end, and a protrusion, and a spring assembly including: a body having a distal channel and a longitudinal slot, the channel being configured to receive the protrusion of the tensioning tube; a spring disposed within the body; and a rod disposed at least partially within the body and connected to the spring. Each of the plurality of sutures may extend axially through the body of the tensioning tube; and a proximal end of each of the plurality of sutures may extend through the longitudinal slot of the body and connect to the rod.

The spring may be a constant force spring. The rod may further include a pin and the pin may be connected to the spring. The longitudinal slot may be open on a surface of the body such that a proximal portion of the tensioning tube and proximal portion of each of the sutures can be placed into the body through the slot. The spring assembly may further include a lock release. The tension lock may include at least one of a button, a sliding switch, or a pin.

A proximal portion of the rod may extend out of the body. The dynamic vascular access and closure device may further include a suture anchor, wherein the suture anchor is configured to attach each of the plurality of sutures to the rod of the spring assembly. The rod may include a recess; and the suture anchor may include a protrusion configured to be received in the recess.

In various scenarios, other method of using a vascular access and closure device can include deploying a plurality of sutures around a vascular access site, inserting an interventional device into the vascular access site, attaching a spring assembly to the sutures, tensioning the sutures using the spring assembly, removing the interventional device from the vascular access site, automatically closing the vascular access site using the tensioned sutures and locking the sutures.

BRIEF DESCRIPTION OF DISCLOSED EMBODIMENTS

Figure 1:
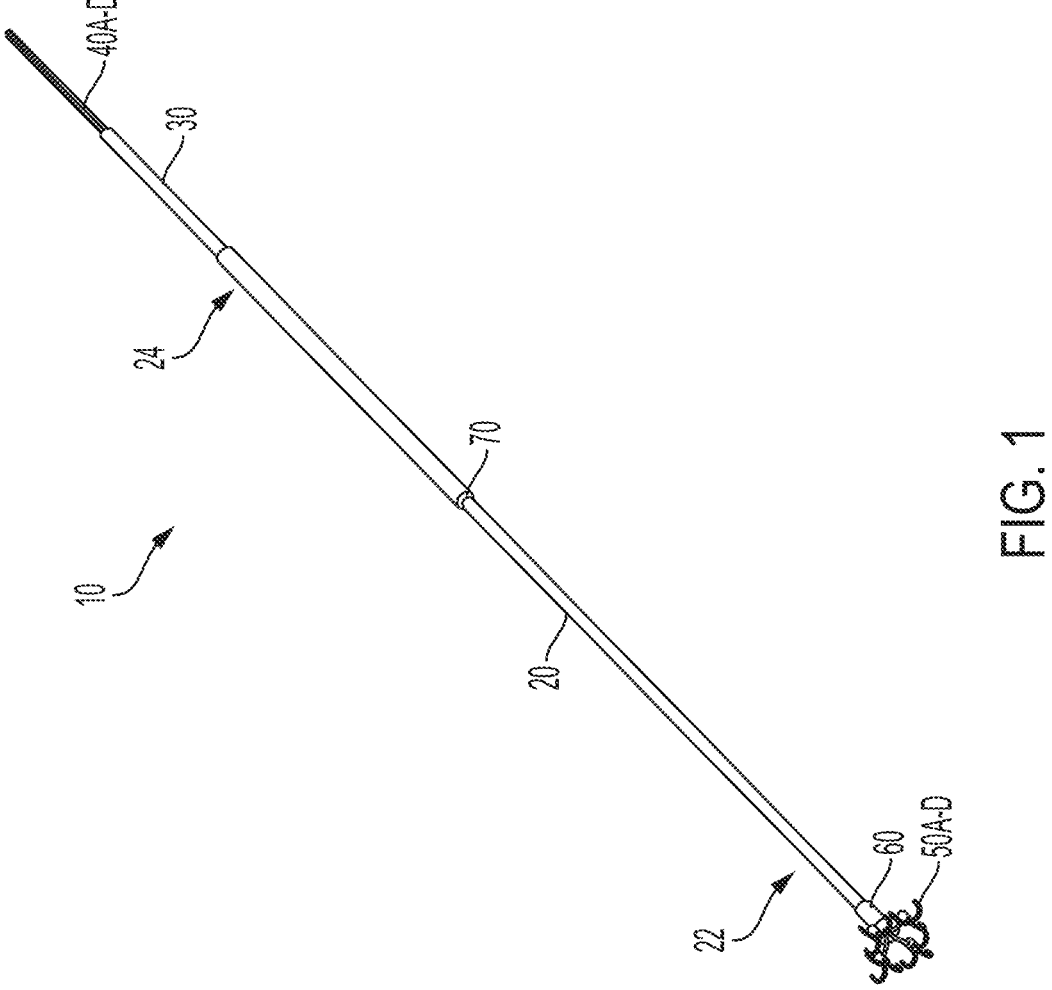
FIG. 1 is a perspective view of an example dynamic vascular access and closure device.

The devices and methods of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, proximal, distal, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". While the examples provided in this disclosure generally relate to percutaneous management of vascular access sites (i.e., in blood vessels), disclosed systems and methods may be used for other management of access sites, such as, but not limited to, access sites in various internal organs. For example, disclosed embodiments may be used for management of access sites to the heart (e.g., inside or outside of the heart) or the gastrointestinal tract.

As used herein, the term "proximal" means closest to the operator (less into the body) and "distal" means furthest from the operator (further into the body). In positioning a medical device from a downstream access point, distal is more upstream and proximal is more downstream.

The term "suture" as used herein can be monofilament or multifilament elongate flexible tensioning devices made of flexible or non-flexible material with sufficient tensile strength for providing a desired force. The suture can be a strand, a wire, a cord, a fiber, a yarn, a filament, a cable, a thread, or the like, and these terms may be used interchangeably. Suture materials may generally be broken into two categories, absorbable (capable of being broken down and absorbed into the body) and non-absorbable (should be manually removed from the body). Example materials include but are not limited to polyglycolic acid, polylactic acid (PLA), polypropylene, polyester, silicone, polyurethane, stainless steel, nickel titanium alloy, nylon, Kevlar fiber, or others.

As used herein, the terms "closure" "closed", "closing" refer to reducing the size (e.g., diameter, area, volume, etc.) of an opening in a biological structure (e.g., a blood vessel) from an initial size to a smaller size.

Medical procedures may require access to the interior space of a blood vessel. This may be achieved using an interventional device such as a dilator or a catheter inserted through the wall of the vessel. In certain procedures, an interventional device may need to be removed temporarily and/or another interventional device may need to be inserted. Because of the opening formed by an interventional device in the vessel wall, there is danger of bleeding when it is removed. Manual pinching of the vessel may be possible, but it requires the physician (and/or assistants) to continuously pinch the vessel before closure and/or before insertion of another interventional device, which may be difficult and still result in some blood loss. Then, the physician still must close the opening after the procedure is complete. Additional blood loss could result during the closure process. Additionally, the interventional device may sever suture threads that are deployed to close the access site in the blood vessel. The devices and methods disclosed herein aim to improve upon at least one of the aforementioned problems. However, it shall be understood that the disclosure herein is not limited to merely solving these specific problems. Additionally, while the devices and techniques disclosed herein are described with respect to a human body or patient, it is understood that the devices and techniques may in suitable circumstances be applied to a non-human patient (i.e., in veterinary medicine).

In various implementations, the current disclosure describes a vessel access and closure device that places cinching sutures in the wall of a blood vessel and creates an access site through the wall of the blood vessel in the area bounded by the cinching suture. One or more interventional devices may be inserted directly through the access site or through an introducer sheath for performing an interventional procedure within the patient's vascular system. Once the interventional device is temporarily and/or permanently withdrawn, the cinching sutures automatically tighten to close the access site into the vessel. Optionally, during deployment of the sutures, the sutures are slack (i.e., do not include tension) in order to avoid severing of the sutures by the interventional device during insertion. Sutures are tensioned after insertion of the interventional device. A suture lock or a knot may, optionally, be used to lock the cinching suture once the interventional procedure has been completed and access to the vessel is no longer needed. The cinching suture also allows for repeated access to the blood vessel while minimizing, inhibiting and/or preventing substances flowing through the vessel opening during and/or after a procedure. The devices of this disclosure can, therefore, decrease resources (e.g., personnel time, materials, etc.) used to control or substantially eliminate bleeding/oozing/exuding fluids. The device can be applied by a wide range of individuals to quickly stem leakage and/or promote wound healing. Disclosed aspects may be employed percutaneously (i.e., without direct visualization of the user). However, it is understood that the devices and methods described herein can also be used under direct visualization by the user or with indirect visualization using, for example, a surgical endoscope.

In addition, the vascular access and closure device of this disclosure allows the use of a single device for providing access to the vessel lumen, irrespective of the diameter of the interventional device. Specifically, the embodiments of this disclosure can be used for interventional devices having a diameter of about 8 French to about 30 French. However, the disclosure is not limited to this range of sizes of interventional devices. In some embodiments, other sizes of interventional devices may be used. For example, devices of certain embodiments may work with size ranges of devices ranging from 12-24 French, 6-12 French, 9-24 French, 10-30 French as well as larger or smaller sizes. Although the devices are discussed in connection with promoting hemostasis, the devices and methods disclosed herein can be used in other applications to achieve different results, for example to provide management of access sites to the heart or gastrointestinal tract. For example, the anchors and sutures of the current access and closure device may be deployed proximate to and/or around an opening in the heart, and may be controlled as disclosed herein for providing access and hemostasis for such opening.

Referring now to the drawings, and in particular to FIGS. 1-5, an example dynamic vascular access and closure device 10 is shown and described. The dynamic vascular access and closure device 10 can be used to facilitate selectable access to the interior of a blood vessel in a body by permitting dynamic opening, closure, and reopening of an access site (e.g., a hole or an opening) in the vessel. As an example, suture anchors may be deployed around the access site in a vessel wall. Sutures connected to the suture anchors may be selectively tightened and relaxed to dynamically open and close the hole via a resilient member disposed within a tensioning tube, as discussed below. In various embodiments, the arrangement of suture anchors (once deployed around a vascular opening) may be configured to enable dynamic and automated radial cinching of a vascular opening by pulling the suture anchors in towards the center of the suture arrangement, where the vascular opening is located (discussed below with respect to FIGS. 19A and 19B). For example, the suture anchors may be deployed in a circular manner around the vascular opening such that when the sutures are tensioned the suture anchors cinch together around the opening (like a purse string). Similarly, the suture anchors may be deployed in a manner that they form approximate vertices of a square, triangle, pentagon, hexagon, or the like with the vascular opening being at an approximate center of the arrangement. However, other arrangements are within the scope of this disclosure such as to allow for linear cinching, or the like.

As shown in the FIGS. 1-5, the dynamic vascular access and closure device 10 includes a tensioning tube 20 having a distal end 22 and a proximal end 24. The distal end 22 is the working end that is placed in proximity to a blood vessel.

One or more suture filaments 40A-D (also, interchangeably referred to as suture wires and sutures) extend axially through the tensioning tube 20 between the distal end 22 and the proximal end 24, where a distal end of each suture wire is coupled to a suture anchor (suture anchors 50A-D). A resilient member 90 and a force applicator 30 are at least partially disposed within the tensioning tube 20.

As shown in the FIGs., the tensioning tube 20 includes an elongate, hollow, tubular outer shaft 201 which defines an inner lumen 202 within which other components can extend through or be placed. While tensioning tube 20 is illustrated as having a circular cross section, other cross sections, such as a square, rectangle, ellipse, etc. are also within the scope of this disclosure. The inner lumen 202 can include a first section 202(*a*) that has a smaller diameter compared to a second section 202(*b*). The smaller diameter of the first section 202(*a*) is large enough to allow the suture wires 40A-D to freely extend through it. The larger diameter of the second section 202(*b*) is large enough to house the resilient member 90 and the force applicator 30 (shown in FIG. 4A). As an example, the smaller inner diameter of the first section 202(*a*) could be about 0.020 inches to about 0.030 inches, while the larger inner diameter of the second section 202(*b*) could be about 0.035 inches to about 0.050 inches. However, other larger and/or smaller dimensions are also possible. For example, the first section inner diameter could change based on the number and/or diameters of sutures and the second section inner diameter could change based on the dimensions of the resilient member.

In various implementations, tensioning tube 20 can include a resilient member stop 70. The resilient member stop 70 can take a variety of forms, such as a step defined by a change in diameter of the tensioning tube from the larger lumen diameter to the smaller lumen diameter (as shown in FIG. 1), a gradual tapering of the tensioning tube 20 from the larger lumen diameter to the smaller lumen diameter, a pin or other structure extending through lumen 202 orthogonal to the main axis of the tensioning tube 20, or other suitable forms.

Tensioning tube 20 may be made from a variety of materials, such as polymers (e.g., plastics, rubber, etc.), metals or alloys (e.g., titanium, stainless steel), or any other suitable material or combination of materials with sufficient stiffness to prevent deformation under the compressive load applied by the tensioned sutures 40A-D.

A force applicator 30 may be an inner biasing tube that is at least partially disposed within the inner lumen 202 at the proximal end 24 of the tensioning tube 20 such that a distal end of the force applicator may reside inside the inner lumen 202 while a proximal end lies outside the inner lumen 202. In various implementations, the force applicator 30 may be a hollow tube. In various implementations, the force applicator 30 may be freely moveable with respect to the tensioning tube 20. While the force applicator 30 is shown as having a circular cross section, other cross sectional shapes can be used, such as a square, rectangle, ellipse, or others. The force applicator 30 and the tensioning tube 20 may have similar or different cross-sectional shapes. Force applicator 30 may also be made from a variety of materials, such as plastics or metals, with sufficient stiffness to prevent deformation under the compressive load applied by the tensioned sutures 40A-D.

A tubular resilient member 90 may be disposed within the tensioning tube 20 between the resilient member stop 70 and the distal end of the force applicator. In various implementations, the resilient member may be a coiled wire such as a spring and/or other types of resilient members that can be compressed against the resilient member stop 70, as discussed below in more detail. For example, the resilient member 90 may be an elastic tube or other structure capable of being repeatedly compressed and decompressed upon application of an axial force on one or both of its ends such as, without limitation, an air spring, hydraulic/gas spring, motor, or any now or hereafter known resilient members. As an example, resilient member 90 may be a linear actuator configured to tension sutures 40A-D. In such an example, the sutures 40A-D may be disposed around the perimeter of the actuator and through the force applicator member 30.

Optionally, the resilient member 90 may be replaced with a suture tensioning motor. In some such embodiments, a force applicator member 30 may not be needed. For example, the interior of tensioning tube 20 could include a motor with a shaft to which the sutures 40A-D could be connected. The shaft can turn to tension the sutures. The motor can be configured to apply a specific amount of torque that could effectively close the vascular opening, but also be overcome by an instrument (e.g., a dilator) separating the suture anchors and expanding the opening.

Figure 4A:
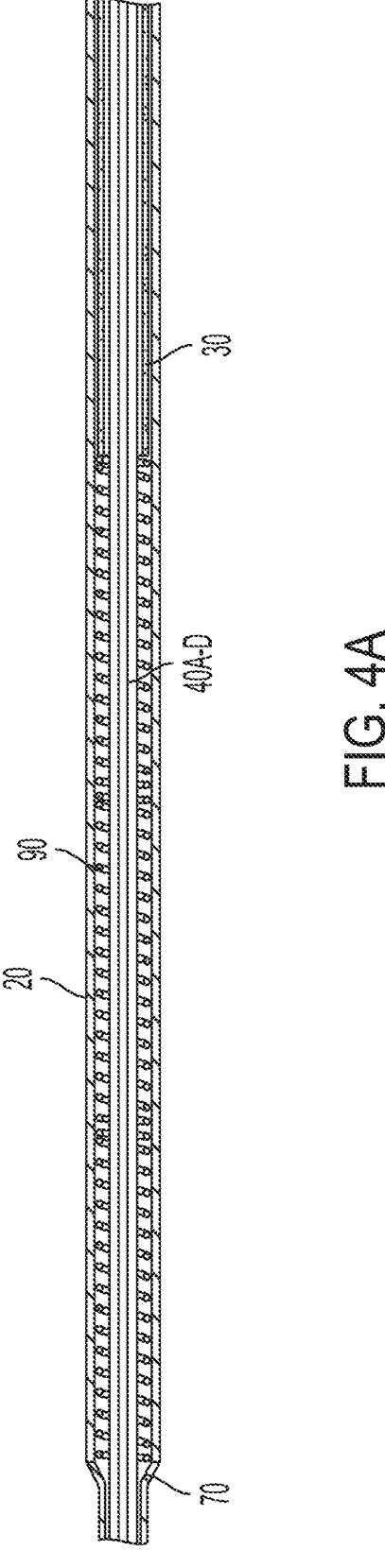
FIG. 4A is a cutaway view of the dynamic vascular access and closure device of FIG. 1 illustrating internals of the device.

FIG. 4A shows a cross-sectional cutaway view of the center of dynamic vascular access and closure device 10. This view illustrates sutures 40A-D extending axially through the length of the tensioning tube 20 and the force applicator 30. Resilient member 90 is disposed between the force applicator 30 and the resilient member stop 70. As illustrated in FIG. 4A, resilient member 90 may be a coil spring or a compression spring and the sutures 40A-D are configured to extend through the coil spring.

In some embodiments, force applicator member 30 may be a tube that also includes an inner step or taper defining a change in internal diameter of the tube (not shown here). The larger internal diameter may be disposed at the distal end of the force applicator member 30 and may be configured to fit around resilient member 90. For example, if resilient member 90 is a spring, the proximal end of the spring may fit inside a recess in the force applicator member 30. Such a configuration can help to reduce or eliminate potential binding of the spring between the tensioning tube 20 and the resilient member 90.

Figure 7:
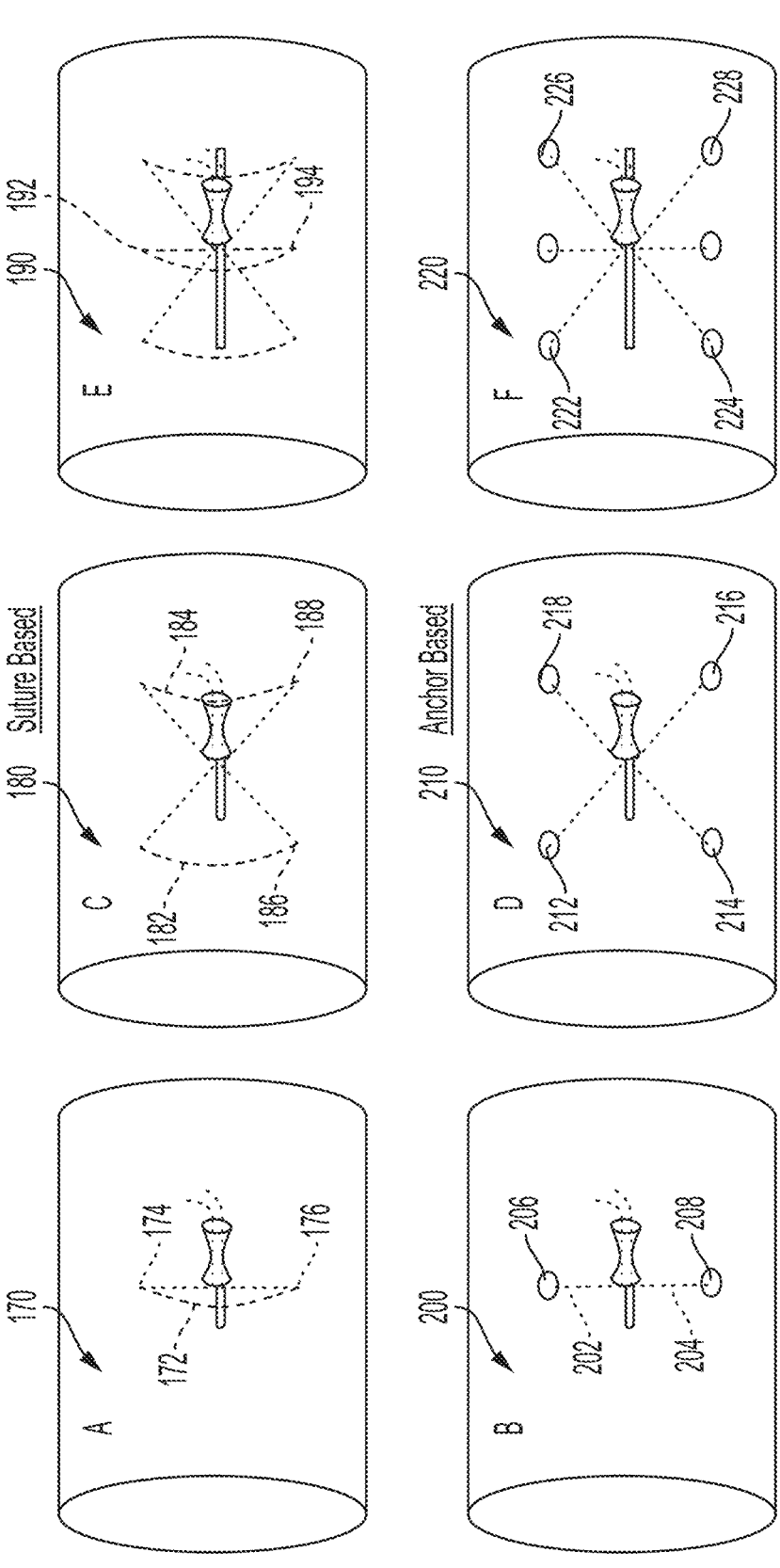
FIG. 7 illustrates various examples of suture placement configurations on a blood vessel wall.

As shown in the figures, suture filaments (or sutures) 40A-D can extend axially through the tensioning tube 20, the force applicator 30, and the resilient member 90. Sutures 40A-D can be monofilament or multifilament thread. A variety of materials can be used for sutures. Suture materials may generally be broken into two categories, absorbable (capable of being broken down and absorbed into the body) and non-absorbable (should be manually removed from the body). Suture materials include but are not limited to polyglycolic acid, polylactic acid (PLA), polypropylene, stainless steel, nylon, or others. While the Figures of the present disclosure illustrate four sutures, in various implementations, more or less sutures may be used depending, for example, on the diameter of the access site and/or an interventional device. For example, FIG. 7 illustrates exemplary embodiments having two, four, and six sutures. The number of sutures and suture anchors may depend on, for example, the size of the vascular access site (which may, in turn, depend on the size of the interventional device to be used). For example, 2 sutures may be used when the diameter of the interventional device is 6-12 French, 4 sutures may be used when the diameter of the interventional device is 12-24 French, and 6 sutures may be used when the diameter of the interventional device is higher than 24 French.

Figure 2:
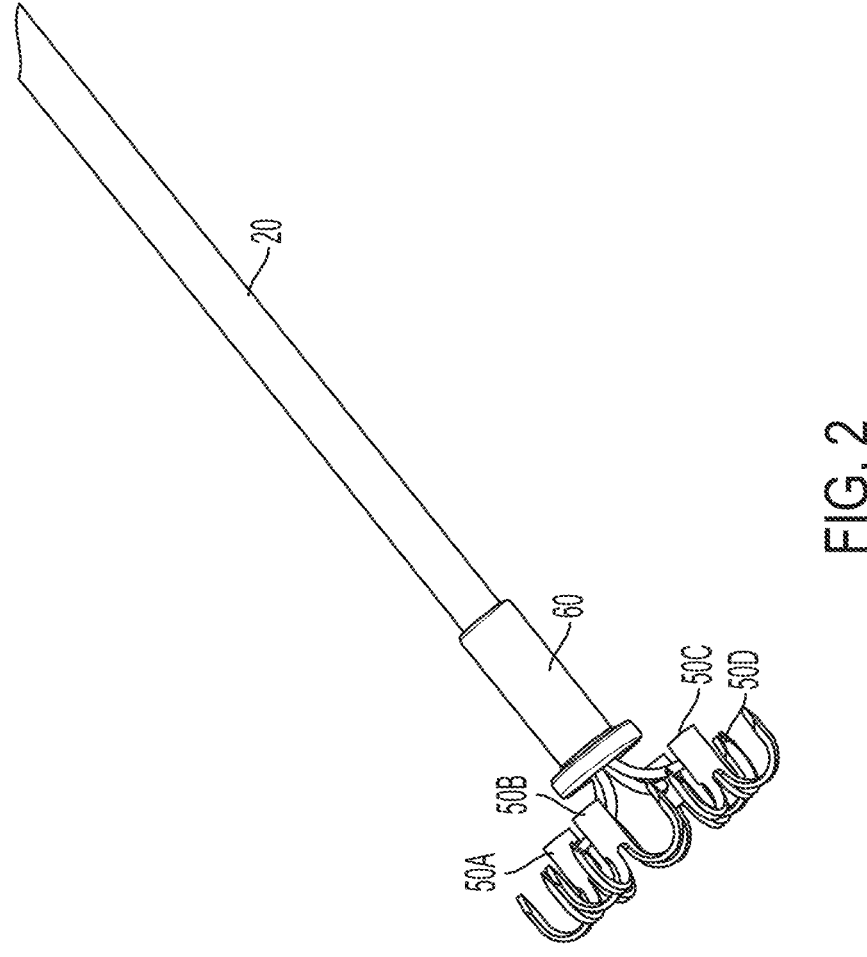
FIG. 2 is an enlarged view of a distal end of the dynamic vascular access and closure device of FIG. 1.

As shown in FIGS. 1 and 2, the distal end of each suture filament is coupled to a corresponding suture anchor 50A-D. Suture anchors 50A-D can be deployed in the surface of a blood vessel to attached the suture 40A-D to the surface of the vessel. Various forms of the suture anchors 50A-D are described below in more detail. Initially, the suture anchors 50A-D are configured to reside within a deployment device so that, as the insertion mechanism (e.g., needle tip) of a deployment device moves through a vessel wall in the distal direction (to create an access site or hole), the suture anchors 50A-D move smoothly forward and outside of the deployment device (without catching on the tissue). Once deployed, the suture anchors 50A-D open or spread, and anchor the distal end of the sutures 40A-D to the vessel wall. The deployment device leaves sutures 40A-D in the vessel wall, as it is withdrawn, anchored by the suture anchors 50A-D. It will be understood to those of skill in the art that any now or hereafter known deployment device can be used for deploying the suture anchors around an access site in a vessel wall. Furthermore, the sutures coupled to the suture anchors may be threaded through the tensioning tube of the device of this disclosure before and/or after deployment of the suture anchors.

In various implementations, a suture lock 60 may be provided for locking the sutures 40A-D upon permanent closure of a vascular access site (described below in more detail). FIG. 2 illustrates distal end 22 of dynamic vascular access and closure device 10 showing a close-up view of suture anchors 50A-D and suture lock 60. As shown in FIG. 2, the distal ends of sutures 40A-D may be fixed to one of suture anchors 50A-D. The suture anchors 50A-D may be deployed upon insertion into the vessel wall to provide a purchase for the suture in the vessel wall.

Suture anchors 50A-D can be made of super elastic or shape memory nitinol material wire(s) and/or tube(s). The nitinol tube(s)/wire(s) may be super-elastic and permit the anchors to assume a compressed state for insertion through the vascular wall without catching on or damaging the vascular wall. For example, the nitinol material wire(s) may be preformed by heat treating into a curvature, for example a hook shape, that will act as a suture anchor as shown in FIGS. 1 and 2. The curvature in the wire(s) can be straightened out by drawing it into deployment device. After the deployment device has advanced to the blood vessel wall, the wire(s) is advanced out and the curvature reforms to anchor the suture. Similarly, nitinol tubes may be laser cut into a hook shape and shape-set by heating the cut tube to a certain temperature. Then, the tubes can be pulled into their original tube shape into the deployment device, then return to their curved hook shape when removed from the deployment device. As an example, the hook formed suture anchors 50A-D of FIG. 2, may be collapsed into a small cylindrical folded shape when residing within the lumen of a deployment device. Optionally, the anchors may be disposed within removable sheaths that may be removed allowing the anchors to return to their hook shape. When the sutures are pulled from the outside of the vessel wall, the hooks will dig into the vessel wall and anchor the distal ends of the suture in the wall.

Figure 5A:
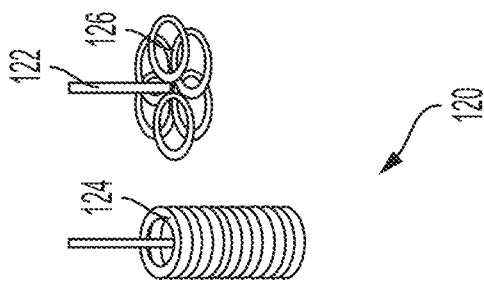
FIG. 5A illustrates various examples of vessel anchors.
Figure 5A:
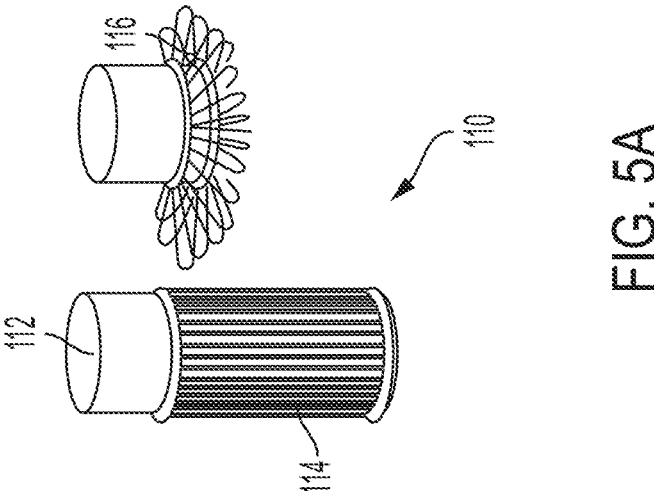
Figure 5A:
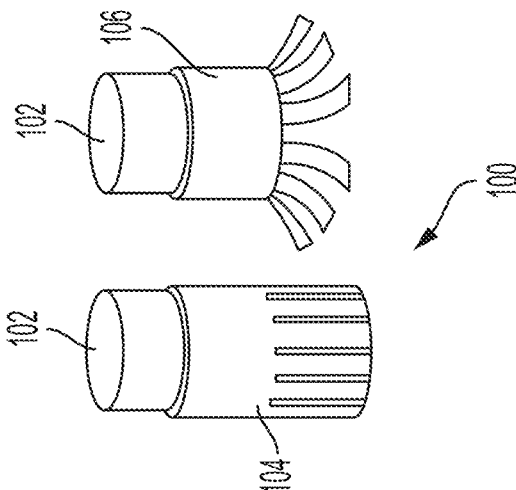
Figure 5C:
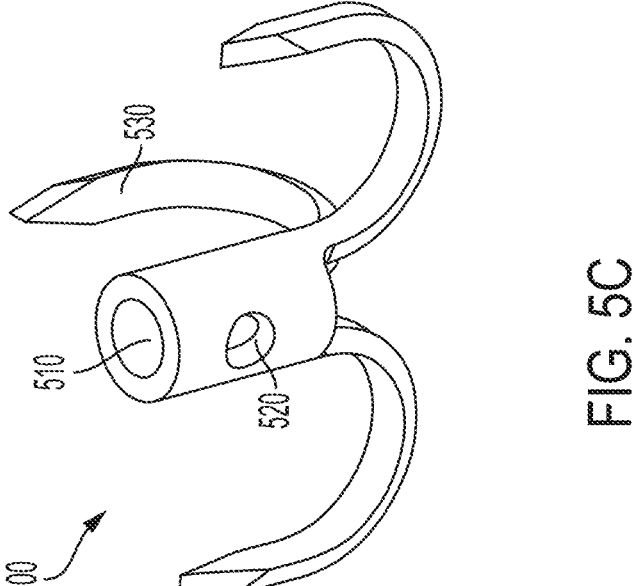
FIG. 5C illustrates an exemplary tube-based vessel anchor in a deployed configuration.
Figure 5B:
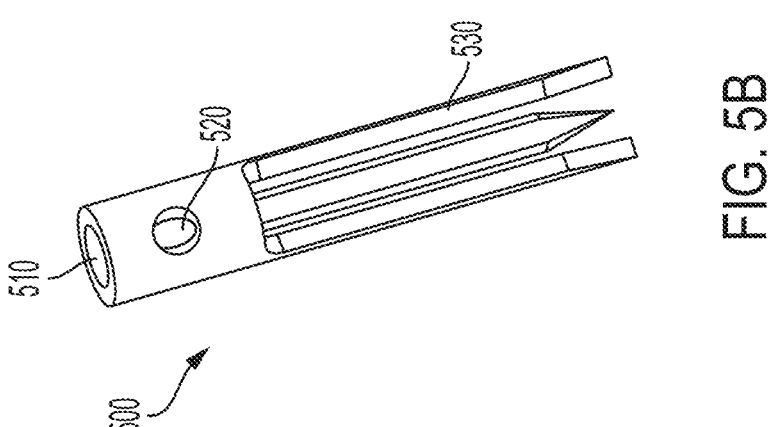
FIG. 5B illustrates an exemplary tube-based vessel anchor.

While the prongs or wires of anchors 50A-D in FIGS. 1-2 are illustrated with three prongs, anchors may have more or fewer prongs. Referring to FIG. 5A, various other types of suture anchors are possible, such as tube-based nitinol anchors 100, wire-based nitinol anchors 110 and suture knot anchors 120. Tube-based anchor 100 is illustrated at the end of suture 102. In a compressed or not expanded form 104, the anchor may be about the same diameter or slightly larger than the suture 102. When the anchor 102 is no longer compressed and is permitted to reach its expanded shape 106, the anchor may have a plurality of hooks or fingers that flare out and contact the interior vessel wall. Another example embodiment of a tube-based anchor is illustrated by FIGS. 5B and 5C, which show a three-prong laser cut tube-based anchor. As described above, a nitinol tube may be laser cut into a hook shape and shape-set by heating the cut tube to a certain temperature. Then, the tubes can be pulled into their original tube shape into the deployment device, then return to their curved hook shape when removed from the deployment device. Tube-based anchor 500 can include a tube body with a bore 510 running therethrough. Prongs 530 and/or hole 520 may be laser cut into the tube. Hole 520 can be used to attach a suture to tube-based anchor 500, as described above. For example, a knot or reflowed suture ball may prevent a suture run through 510 from pulling back through hole 520. After tube-based anchor 500 is cut, it may heat formed in to the hook shape illustrated in FIG. 5C. For example, prongs 530 may be formed into hooks that can engage with a vessel wall. Tube-based anchor may then be compressed (e.g., a shape such as that illustrated by FIG. 5B) inside a deployment device. When released from the deployment device, tube-based anchor 500 can return to deployed hook shape illustrated in FIG. 5C.

Referring back to FIG. 5A, similarly, wire-based anchor 110 may have a compressed form 114 (e.g., when it is inside a tube for deployment) and in an expanded form 116, have a variety of small wires that spring out and contact the vessel wall. Non-anchor-based sutures may similarly be used without deviating from the principles of this disclosure. For example, sutures can be tied with one another and form a knot by going over themselves within tissue to close the opening. In other examples, a suture knot in low profile could be delivered within the tissue and then pulled to form a larger knot that can act as an anchor. For example, suture based anchors 120 may include a cylindrical knot of suture 124 that is inserted into the interior of the vessel. When the length of suture 122 is pulled on to tension the suture 122, the knot 124 can be pulled into an expanded form 126, which can contact the interior of the vessel wall. While the anchors of FIG. 5 are described as either nitinol or suture-based anchors, anchors may be made from other suitable materials. Such vessel anchors can provide other advantages in addition to ease of deployment and relative strength. For example, in elderly patients, the patient's vessels are often calcified, making it more difficult for traditional sutures to be placed across the vessel in a percutaneous manner. Disclosed vessel anchors may still penetrate the calcified vessel wall, permitting more simple vessel closure than would otherwise be possible without the anchors.

In some examples, one or more of the anchors may have additional features to facilitate radial cinching of an opening. For example, a hole (or any other opening) may be provided on a side of an anchor for suture exit, where a suture exiting from a side (e.g., radially) when tensioned will create a radial or sideway force instead of an outward pulling force.

Though not illustrated in FIG. 5, other types of anchors are also possible, such as pledget-based anchors. Pledget-based anchors may include a suture that loops through the vessel wall and is tied or otherwise fixed to a pledget on the outside of the vessel wall. In this example, the pledget can serve both as a point for the suture to be affixed to and reinforcement for the vessel wall. In some embodiments, sutures 40A-D, anchors 50A-D, and suture lock 60 may be dissolvable inside the body of the patient. One or more of the sutures 40A-D, anchors 50A-D, and suture lock 60 may be constructed of a body-absorbable material (such as, but not limited to, PLA) that will break down inside the human body.

While the figures illustrate anchor-based sutures, the disclosure is not so limiting and non-anchor based sutures may similarly be used without deviating from the principles of this disclosure. Optionally, sutures 40A-D may not include an attachment device or anchor to a vessel wall (e.g., for use with older patients who have calcified/thicker vessel walls making it difficult for use of anchor-based sutures). Instead, the suture may be inserted into the vessel, extend through a portion of the Interior space of the vessel, and exit at a different location on the vessel. Such an arrangement of non-anchor based suture attachments is also illustrated by FIG. 7 (e.g., as illustrated by suture attachment arrangements 170-190 in FIG. 7). In some embodiments, in which anchors are not used, the sutures may pass through the vessel and attach back to the tensioning tube.

Figure 3:
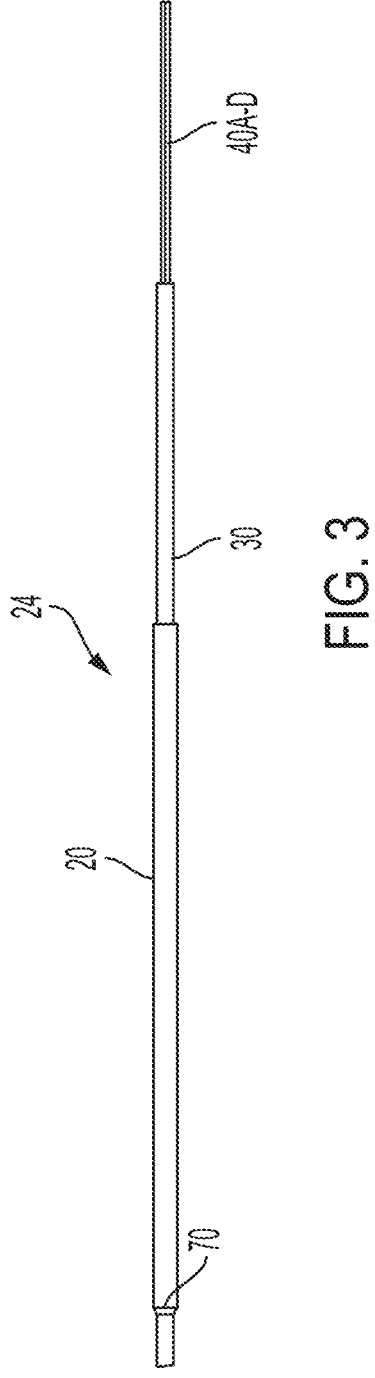
FIG. 3 is an enlarged view of a proximal end of the dynamic vascular access and closure device of FIG. 1.

The sutures 40A-D may also include a suture stop at or near the corresponding proximal ends. FIG. 3 illustrates the proximal end of 24 of the tensioning tube 20, with the proximal end of sutures 40A-D being exposed at the proximal end of force applicator member 30. A suture stop may take a variety of forms, including but not limited to, a knot tied in the sutures, a ferrule crimped onto the sutures, a reusable suture lock (such as that illustrated in FIG. 9), or other suitable alternative. Consistent with disclosed embodiments, the suture stop may be made of a variety of materials including suture material, plastics (e.g., PLA), titanium, etc. Optionally, a suture stop may also be an attachment and/or coupling to the tensioning tube body.

The suture stop is provided such that the length of the sutures 40A-D between the suture anchors 50A-D and the suture stop remains constant at all times. Furthermore, the suture stop is locked into a fixed position with respect to the resilient member 90 and/or the force applicator 30 such that the suture stop is configured to cause compression or release of the resilient member 90 between the force applicator 30 and the resilient member stop 70. When the sutures and suture anchors are initially inserted into a vessel access site, the resilient member 90 is in a semi-depressed state (and/or a resting state), and the access site is cinched closed by the sutures 40A-D (the length of the sutures 40A-D between the suture anchors 50A-D and the suture stop and/or the semi-depressed state of the resilient member is configured to cause the cinching). However, when an interventional device (e.g., a catheter, a dilator, a sheath etc.) is inserted through the access site, as the access site diameter increases, the sutures 40A-D are pulled apart and tensioned such that the suture stop causes further compression of the resilient member 90. In the tensioned state the sutures may cause the vessel membrane at the access site to close around the interventional device minimizing leakage during access to the vessel lumen, while the access site opening is expanded as needed to permit interventional device entry into the vessel lumen. As soon as the interventional device is removed from the access site, the access site diameter decreases and the kinetic energy stored in the depressed resilient member 90 is released causing the sutures 40A-D cinch the access site and the resilient member 90 moves back to its semi-depressed state (and/or resting state). As such, the vascular access and closure device 10 provides a dynamic vascular access via an access site that allows an interventional device to be repeatedly inserted to the access site while automatically closing the access site (temporarily and/or permanently) in the absence of the interventional device.

Figure 4B:
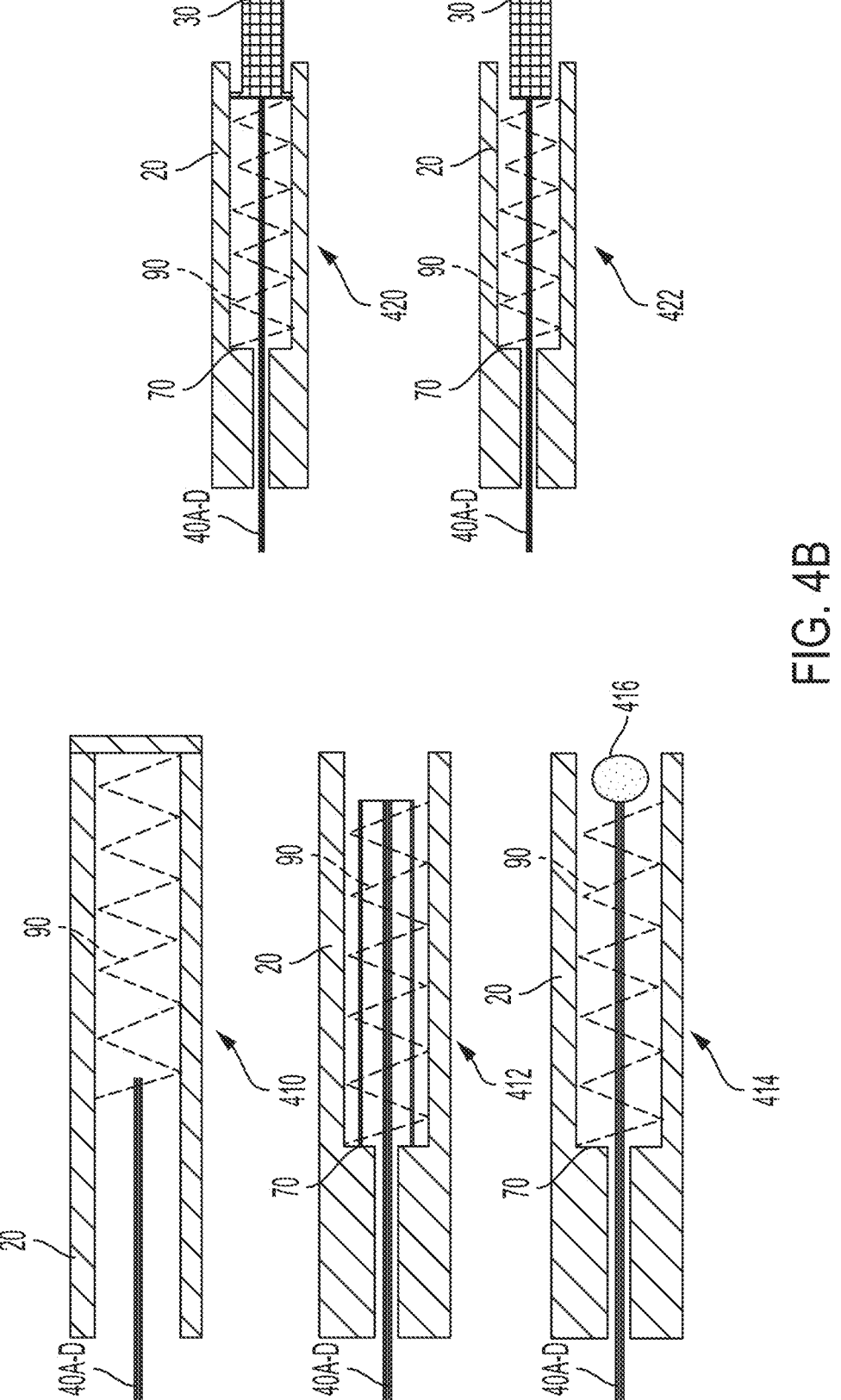
FIG. 4B illustrates cutaway views of alternative arrangements of a dynamic vascular access and closure device.

Referring to FIG. 4B, other alternative configurations of the tensioning tube, the resilient member, the resilient member stop, and/or the force applicator may be used. In some embodiments, the tension in the sutures may not be adjustable based on factors other than the resilient member spring force (e.g., as described below with respect to configurations 410, 412, and 414). In some other embodiments, the tension in the sutures may be adjustable based on other factors in addition to being dependent on the resilient member spring force (e.g., as described below with respect to configurations 420 and 422).

For example, configuration 410 can include a proximal end of the sutures 40A-D being directly coupled to or attached to a portion of resilient member 90 (e.g., close to or at the distal end), with the proximal end of the resilient member 90 being attached to a closed proximal end of tensioning tube 20. In such embodiments, a force applicator or a resilient member stop may not be provided. Rather, in such configuration 410, the resilient member 90 is configured to be put under a resilient force (e.g., in tension) by extension against the closed proximal end of the tensioning tube 20 compared to the resting state of the resilient member. For example, the suture length may be configured such that the resilient member is extended when the access site opening is expanded for insertion of an interventional device. The resilient member automatically returns to its resting state when the interventional device is removed thereby cinching the access site closed. Other non-adjustable configurations, such as configurations 412 and 414 can place resilient member 90 under compressive force when the access site opening is expanded for insertion of an interventional device. For example, in configuration 412, sutures 40A-D may extend axially through the center of resilient member 90, loop around the proximal ends of resilient member 90, then double back and attach to an inner surface of tensioning tube 20, for example, at resilient member stop 70. Thus, in configuration 412, when sutures 40A-D are pulled on at the distal end due to expansion of the access site opening, sutures 40A-D will cause compression of resilient member 90 against resilient member stop 70. The resilient member automatically returns to its resting state when the interventional device is removed thereby cinching the access site closed. It should be noted that in the configuration 416, a compression of the resilient member 90 by a distance "x" cause "2x" lengthening of the attached sutures. As another example configuration, configuration 414 can include a suture stop 416, such as a knot, ball, crimped stop, or other suitable member at the proximal end of the resilient member 90. In this configuration, the sutures 40A-D can extend axially through resilient member 90, with stop 416 contacting resilient member 90 and transferring tension in sutures 40A-D to resilient member 90 causing compression of the resilient member when the access site opening is expanded.

As discussed above, configurations 420 and 422 illustrate embodiments where the tension in the sutures is also dependent on factors additional to the spring force of the resilient member. For example, the tension in the sutures can be adjusted by moving the position of a force applicator 30 relative to sutures 40A-D within the tensioning tube 20, thus allowing more tension or less tension to be applied to sutures 40A-D by resilient member 90. In both configurations 420 and 422, sutures 40A-D can run axially through resilient member 90 and are coupled to a force applicator 30 that is moveable with respect to the sutures within the tensioning tube. For example, force applicator 30 can be a tube or ferrule that is crimped on to sutures 40A-D in a manner than permits sliding of force applicator 30 on sutures 40A-D. In the examples of FIGS. 4B, by sliding force applicator 30 to the left, a user may compress resilient member 90 and thus increase the tension placed on sutures 40A-D during use. For example, in some cases, additional cinching force may be required to fully stop bleeding (i.e., a force greater than that allowed by the resilient member itself), and a user may increase the suture tension via adjustment of the force applicator position with respect to the resilient member. Conversely, if force applicator 30 is slid to the right in FIG. 4B, force applicator 30 can expand and less tension can be placed on sutures 40A-D. In some embodiments, as shown by configuration 420, resilient member 90 may also be attached to force applicator 30. In other embodiments, as shown by configuration 422, force applicator 30 may not be attached to the resilient member 90. Thus, the user may employ the adjustability of the position of the force applicator with respect to the resilient member to further dynamically tune the cinching force based on a particular application (i.e., in addition to that provided by the resilient member). For example, a larger access site or larger vessel may require a larger cinching force (i.e., higher suture tension) to stop bleeding as opposed to a comparatively smaller access site or vessel.

In some embodiments, the resilient member 90 may be modular. For example, resilient member 90 may be removable from tensioning tube 20. Different strengths or sizes of resilient member 90 can then be interchanged within the system to provide tensioning for different applications. Resilient member 90 may also be modularly attached to a tensioning tube 20, in which sutures 40A-D are preinstalled. In yet another embodiment, the sutures may be fed into the tensioning system after of sutures are placed.

Optionally, when the access site is closed by cinching of the sutures 40A-D, a guide wire may continue to extend from the access site. When access into the vessel is desired, a new interventional device, may be placed over the guidewire and pushed into the opening. Optionally, a guidewire may not be present and the tensioning tube 20 may be used as a positioning tool for guiding an interventional device towards the access site.

In some example embodiments, the suture stop can be coupled to the proximal end of the force applicator member 30 and prevent the proximal end of the sutures 40A-D from sliding through force applicator member 30 beyond the stop. Thus, when the sutures around the access site are pulled apart, the suture stop will tension the sutures 40A-D, and cause compression (or extension) of the resilient member 90, via the force applicator 30. In some embodiments, the force applicator member 30 may comprise the suture stop. For example, the force applicator member 30 may be crimped or pinched at or near its proximal end, while the sutures 40A-D are inside. Such crimping can cause the force applicator member to grip onto the sutures and act as a suture stop. In further embodiments, the force applicator member may include a stop feature such as a hook or a thin notch, which could interface the sutures to fix the sutures to the resilient member. For example, the proximal end of the tubular wall of the force applicator member 30 may have a thin slit or notch cut into it angled relative to the main axis of the tube. The sutures 40A-D could be slide into this notch to inhibit their movement relative to the force applicator member 30. Similarly, force applicator member 30 can include a hook or other feature around which the sutures 40A-D could be wrapped or tied to fix them to the force applicator member 30.

One of ordinary skill will understand that the level of tension placed on the sutures 40 can be varied in several ways. The tension on the sutures 40 may be affected at least by the relative strength of the resilient member 90; spring constant of the resilient member 90 (i.e., if it is a spring); the relative lengths of the sutures 40A-D the tensioning tube 20, the resilient member 90, and the force applicator member 30; type of suture material (e.g., the amount the suture material will stretch); the location of the resilient member stop 70 within the tensioning tube 20; user adjustment of force applicator 30 (in adjustable tension configurations);or the like. In the various embodiments described herein, the tension placed on sutures 40A-D can fall within various ranges such as from 0.1 to 4 pounds, from 0.1 to 2 pounds, or from 0.25 pounds to 2 pounds or others. Required cinching force may depend up on the application. For example, a femoral artery will require different cinching force than a femoral vein because the pressure inside the vessels may be different.

Referring back to FIGS. 1-2, the distal end 22 of tensioning tube 20 may, optionally, include a suture lock 60. Suture lock 60 can hold the sutures 40A-D in tension to keep the access site permanently closed when additional access to the vessel lumen is no longer needed and the tensioning tube 20 has been removed. Additionally and/or alternatively, the suture lock may be placed onto the sutures 40A-D after the have been removed from the tensioning tube when additional access to the vessel lumen is no longer needed. Such permanent or semi-permanent closure can permit the access site to heal and prevent addition bleeding until healing is complete. As illustrated by FIG. 2, suture lock 60 can be a ferrule that slides over the sutures 40A-D. This ferrule can be crimped, causing it to be crushed around and grip the sutures, holding them in place. Optionally, the suture lock 60 may contact the tensioning tube 20, but can still be crimped while the tensioning tube is in place, thus securing the sutures 40A-D in a tensioned position. After crimping of suture lock 60, the user could then cut the sutures 40A-D at the proximal end of the suture lock 60. This would then separate the anchors 50A-D, distal end of the sutures 40A-D, and suture lock 60 from the rest of the dynamic vascular access and closure device 10 and permanently close the access site. The locking mechanisms (e.g., suture locks) may be separate from or integral with any part of the device 10. They may be removably or fixedly mounted on the device 10 (and/or its components) and/or another device. In some examples, the suture lock is disposed at or near the distal end of the tensioning tube 20, and may be advanced over the tensioned sutures to a location between the distal end of the tensioning tube and the access site. The suture lock when advanced may, optionally, provide additional inward radial cinching force on the anchored sutures. Optionally, a suture lock is included and/or advanceable over the tensioning tube 20 and/or the sutures such that the suture lock can be appropriately positioned over the sutures to be locked.

Figure 6A:
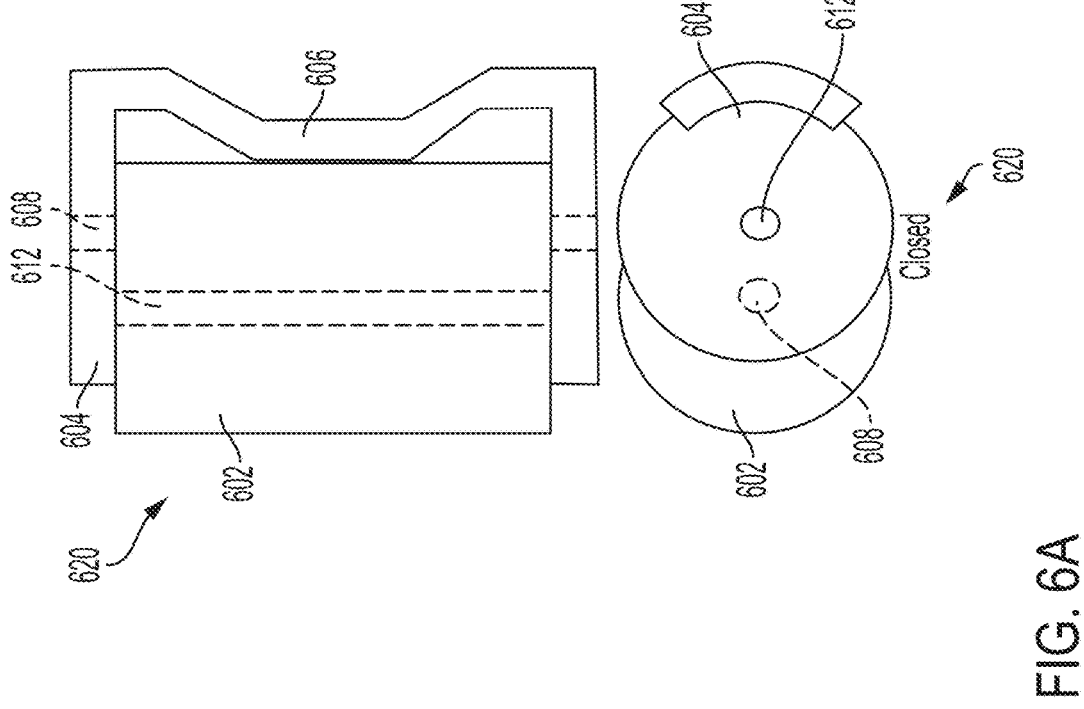
FIG. 6A illustrates an example of a semi-permanent suture lock.
Figure 6A:
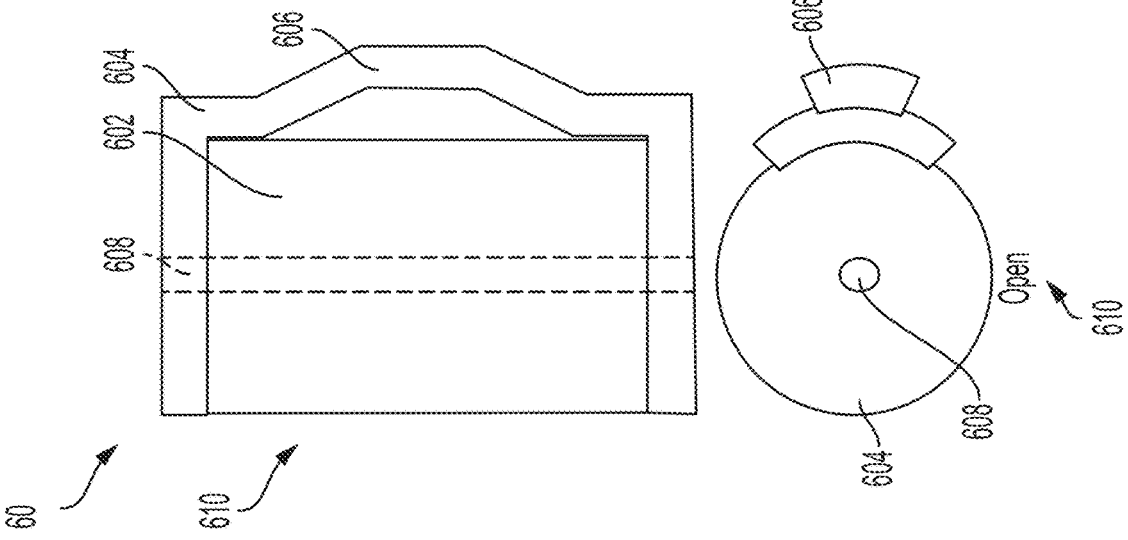

As described herein, suture lock 60 may take any now or hereafter existing form without deviating from the principles of this disclosure. One such example of a suture lock 60 is illustrated by FIG. 6A. FIG. 6A illustrates a selectable suture lock with an open position 600 and a closed position 620. As shown by the illustrated side and top views, the suture lock can include an inner body 602 and outer shell 604 disposed around inner body 602. Inner body 602 can be slideably connected to outer shell 604. Outer shell 604 may include a hole 608 extending through the top and bottom of outer shell 604. Inner body 602 can include a bore 612 that runs completely through inner body 602. In open position 600, holes 608 can be aligned coaxially with bore 612 to permit sutures to be placed through the suture lock. Outer shell can include a toggle 606 that can be used to displace inner body 602 relative to outer shell 604 to place the suture lock into closed position 620. When toggle 606 is pushed and moved transversely to the axis of bore 612, it can move inner body 602 transversely relative to outer shell 604. Thus, in closed position 620, holes 608 and bore 612 can be misaligned. The misalignment can trap sutures between inner body 608 and outer shell 612 to lock the sutures in place and prevent movement of the suture lock along the sutures.

Figure 6B:
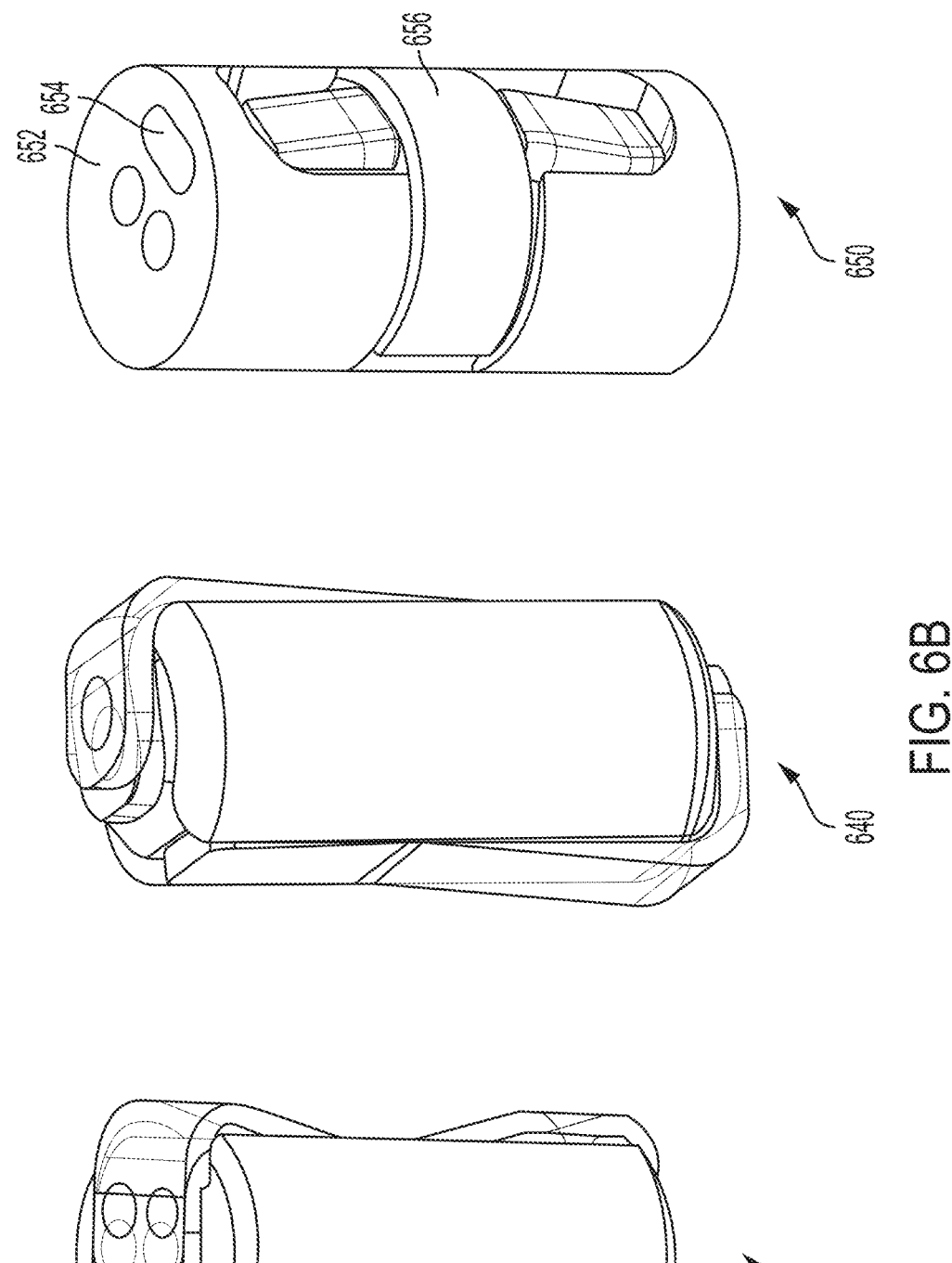
FIG. 6B illustrates additional exemplary semi-permanent suture locks.

FIG. 6B illustrates other exemplary sutures locks. For example, suture locks 630 and 640 are a two-component selectable suture locks with two channels through which sutures may be extend. When the two-component lock is in a closed position, two locking members will pinch the suture and prevent the suture from slipping through the lock. In an open configuration, the channels are aligned and the sutures are free to move. When placed into a closed configuration, the channels can mal-aligned, preventing the sutures from moving freely. In some embodiments, in the event that the access site would need to be accessed again after the suture lock was tightened, the suture lock may be unlocked to permit free movement of the sutures. Lock 630 includes two separate bores for sutures, while lock 640 contains a single bore through which sutures can extend.

Lock 650 of FIG. 6B illustrates a 3 component suture lock design. Lock 650 includes a body 652 with two holes an open bore, the open bore can allow sutures to freely move through it. A stop element 654 that can be moved inside the channel to block the free movement of the sutures. The stop element can be moved from a closed position to an open position with toggle 656. While lock 650 is illustrated with two holes for sutures, more or fewer holes could be used.

Other types of suture locks are possible. For example, a suture lock could also take the form of a single body, single channel lock, for example, a ferrule made of metal which is crimped irreversibly at the end of the procedure to lock the distal end of sutures under tension.

FIG. 7 illustrates various example arrangements of suture placement on a blood vessel wall, consistent with disclosed embodiments. Examples 170, 180, and 190 show non-anchor based suture placement. As illustrated in FIG. 7, non-anchor based suture attachment may include a suture loop running inside the vessel. In the case of arrangement 170, a suture filament 172 may have entry/exit points 174,176 spaced out transversely on the surface of the blood vessel. The distance between the points may vary based on, for example, the size of the vessel, the size of the suture, the size of the interventional device being introduced into the vessel lumen, etc. The suture may be looped through the vessel such that when the free ends of the suture outside of the vessel are pulled, the entry points of the suture are pulled together, thus closing the access site opening between the two entry points. Example 180 depicts a four point closure arrangement with two sutures. The two sutures 182, 184 can each have a transversely spaced entry/exit points. The two sutures can also be spaced axially along the vessel. For example, in arrangement 180, entry holes 186, 188 are axially spaced on the vessel. The transverse spacing between the entry/exit points of the two sutures may be substantially the same. Similarly, the axial spacing between the two sutures may be substantially the same as the transverse spacing between entries and exists, causing the four pulling points of the sutures to form a square on the vessel. Example arrangement 190 of FIG. 7 is a six point closure arrangement using three pieces of suture. Just as with arrangements having fewer points, the points of each suture can be transversely spaced apart. For example, entry points 192, 194 of the middle suture in arrangement 190 are transversely spaced. Additionally, the out sutures of arrangement 190 can be spaced along the main axis of the vessel. As shown in arrangement 190, even with greater than four points of attachment to the vessel, the tensioning tube 20 assembly can remain in the center of the points to ensure proper closure and substantially equal tension on each of the sutures. While the Figures generally depict symmetric arrangements of sutures, arrangements need not be symmetric. Additionally, while FIG. 7 illustrates arrangements having 2, 4, or 6 sutures, other numbers of sutures (including an odd number of sutures) can be used.

FIG. 7 also illustrates examples of anchor-based suture arrangements. For example, rather than using one piece of suture extending through the vessel and out of another point in the vessel, multiple pieces of suture can be used, each having an anchor disposed on the distal end. As described herein, the anchor can attach to the vessel wall. The sutures can then be pulled tight to draw the anchored ends together and close a vascular opening or access site. In an example arrangement 200, two sutures 202, 204 are used with anchors 206, 208, respectively. Anchors 206, 208 are placed on a transverse axis through the vessel and are spaced apart on that axis. Arrangement 210 uses four anchors 212, 214, 216, 218 spaced apart in a square pattern, with each anchor having its own attached suture. Similarly, arrangement 220 uses six anchors. In some embodiments, as shown in arrangement 220, arrangements may have more than four anchors, but still have a substantially square pattern. In this case, the spacing between corner anchors 222, 224, 226, 228 is substantially the same, creating a square, even though two additional anchors are disposed between anchors 222, 226 and anchors 224, 228. As noted above with respect to non-anchor suture patterns, having a symmetric pattern of anchors can permit the tensioning tube 20 assembly to be disposed in the center of the anchors to ensure proper closure and substantially equal tension on each of the sutures. Other suture arrangements and number of sutures (e.g., circular, star-shaped, etc.) are also within the scope of this disclosure.

The choice of suture arrangement may depend on, for example, the size of vessel being accessed and/or the size of the interventional instrument being used. Larger vessels and dilators may present a greater potential risk of bleeding to the patient. Smaller vessels may also have limited space to accept sutures or anchors, thus limiting the number or type of arrangement of sutures. As an example, a large catheter having a size of 24-30 French might require an arrangement of six anchors, such as 220. A smaller catheter, for example, a size of 12-24 French, may require less anchors, such as a four anchor arrangement 210. Even smaller catheters (e.g., those used in some arterial applications having a size of 6-12 French) might only require a linear two suture pattern, such as that of arrangement 200.

Figure 9:
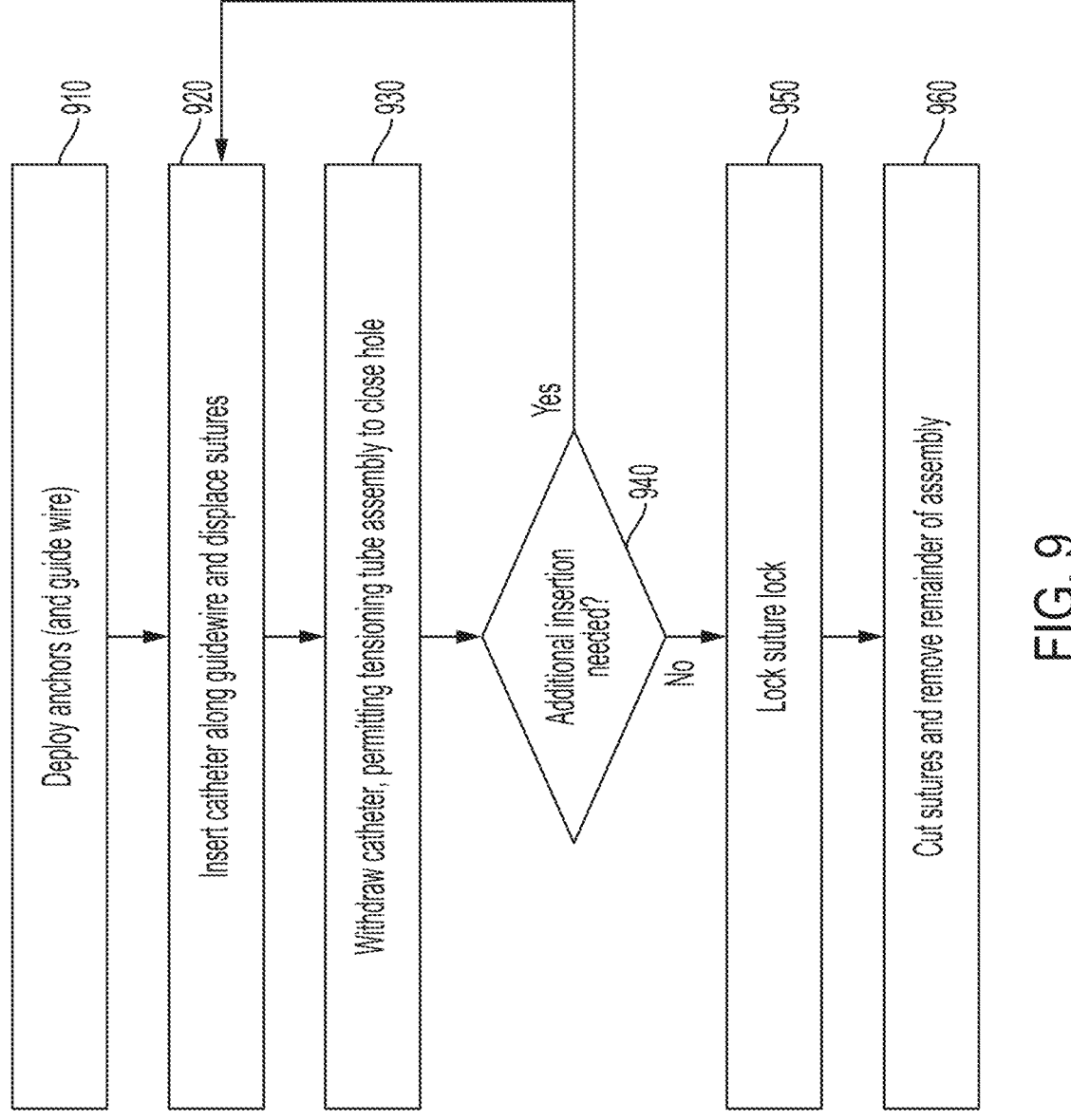
FIG. 9 is a flowchart illustrating an example method of using a dynamic vascular access and closure device.

FIG. 9 is a flowchart depicting an example method 900 for using a dynamic vascular access and closure device 10 of this disclosure. At step 910, the anchors and/or sutures may be deployed into the vessel wall using any now or hereafter known deployment devices. Step 910 may also include deploying of a guide wire. At this step, the dynamic vascular access and closure device can tension the sutures around the guidewire and/or an access site or hole in the vessel.

At step 920, method 900 may include inserting an interventional device over the guide wire into the vessel. In other embodiments, the sutures and tensioning device could be deployed before a vascular access. Accordingly, the anchors may be placed without a guidewire and the guidewire can be inserted after the placement of the device. As described herein, when the interventional device is inserted, the suture may be displaced or pulled, permitting the access site in the vessel to expand. The force applied to the sutures by the interventional device can cause a compression (or, in applicable embodiments, extension) of the resilient member within the tensioning tube. The force applied by the resilient member to the sutures will hold the anchors close to the instrument, sealing the vessel wall around the periphery of the instrument and preventing or reducing any unwanted bleeding. At step 930, the interventional device may be withdrawn from the vessel. As the instrument is withdrawn, the access hole will be closed by the sutures automatically as the resilient member is decompressed, which in turn can push on the suture stops and cause the sutures to cinch together. This automated closure of the access site can prevent bleeding when the interventional device is removed from the vessel. Such automated bleeding prevention is a significant improvement over the existing techniques because a user is not required to manually pinch the vessel to prevent the bleeding. Other times, a physician may need to employ a cross-over balloon, which can be balloon inserted from another access site and inflated temporarily to stop bleeding. The automated cinching provided by disclosed embodiments may mitigate the need for such a technique. Accordingly, through use of the dynamic vascular access and closure device, the procedure is made both easier for the surgeon and safer for the patient.

As described herein, the dynamic vascular access and closure device 10 of the disclosure also allows for reinsertion of an interventional device through the same access site. Accordingly, method 900 may include a determination at step 940 of whether an additional interventional device insertion is needed. If an additional interventional device insertion is needed, step 920 may be repeated. If an addition interventional device insertion is not need, step 950 may be executed. At step 950, the suture lock can be locked. As described herein, the suture lock may be locked by crimping a ferrule or locking a selectable lock, among other ways. At step 960, the sutures may be cut. The sutures maybe cut at any desired position, such as the distal end of the tensioning tube between the tensioning tube and the suture lock, leaving a relative minimum amount of extra suture attached to the patient's vessel. The tensioning tube assembly may be removed thereafter. In other embodiments, the suture could be cut at the proximal end of the resilient member, between the resilient member and the suture stop leaving a longer length of extra suture protruding from the suture lock (which may be used to tie a knot at the end of the suture lock to provide additional safety against unraveling of the sutures).

Figure 8:
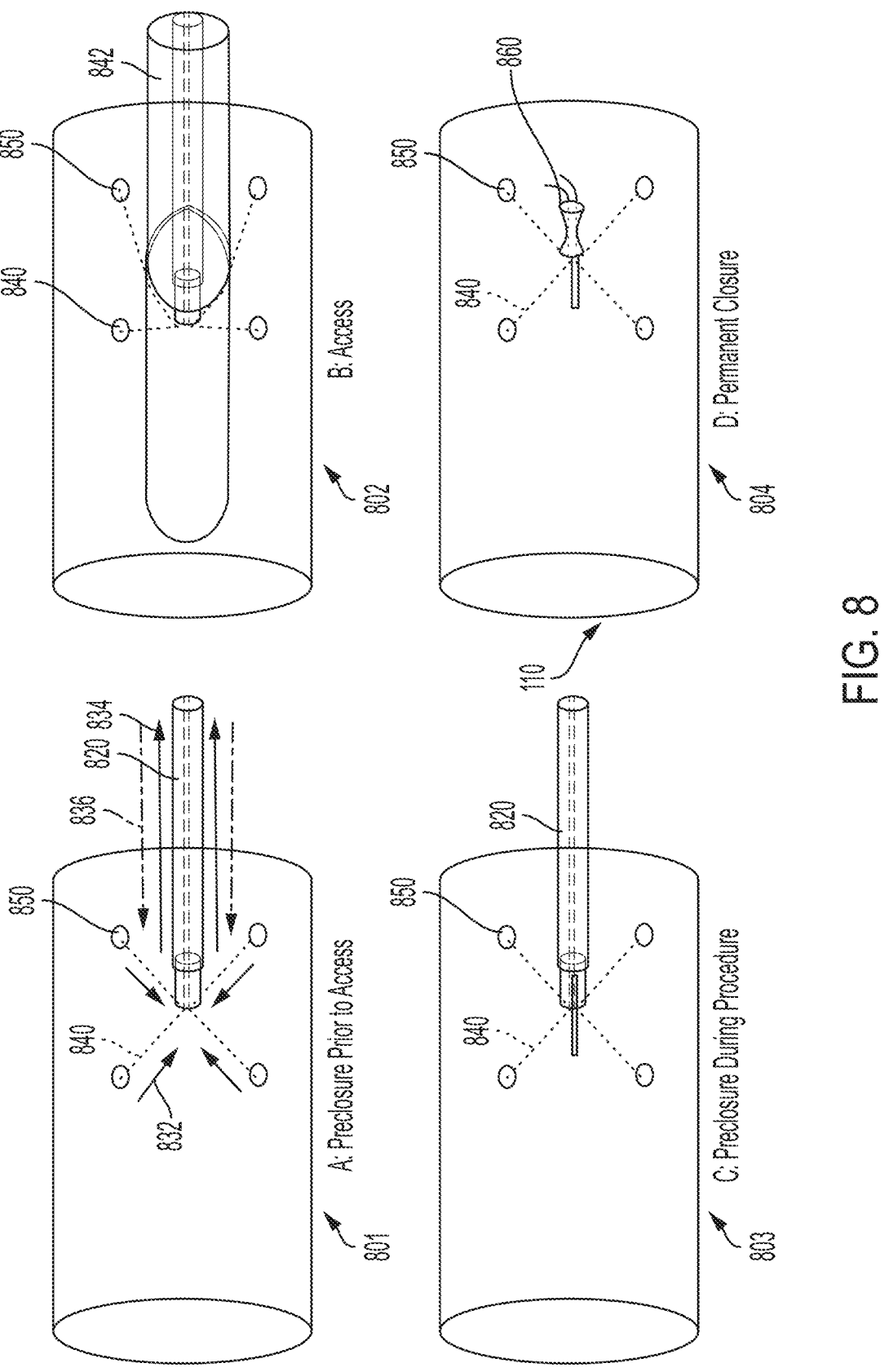
FIG. 8 is a schematic diagram illustrating an example method of using a dynamic vascular access and closure device.

FIG. 8 provides a visualization of the above process of using the dynamic vascular access and closure device 10 to provide access to a vessel lumen via an access site. The example in FIG. 8 shows four anchor-based sutures attached to a vessel around an access site 800. Illustration 801 shows the 4 sutures (collectively, 840) anchored in the vessel wall, via anchors (collectively, 850), while the access site 800 is cinched closed. The sutures 840 extend through a suture lock 860 and the tensioning tube 820 (including the components discussed above). Arrows 832 and 834 show the direction of cinching force applied by the sutures around the access site. As described above, this force can be a radial force drawing each of the anchors 850 toward the access site that is located between the anchors. Arrows 836 show the direction of the reaction force on the tensioning tube that pushes it towards the vessel wall. While FIG. 8 illustrates the anchors 850 being positioned in a substantially symmetrical configuration with respect to the access site, the disclosure is not so limiting, and the anchors can be placed in any suitable position. When the anchors are positioned in a substantially symmetric arrangement, and the sutures have approximately the same length, the tensioning tube 820 is centered between the anchors such that an approximately equal tension is applied in the sutures. In some embodiments, a guide wire (not illustrated) may be inserted into the access site 800 during anchor deployment. This guide wire may then be used to guide insertion of interventional devices into the access site. Optionally, a guidewire may not be present and the tensioning tube 820 may be used as a positioning tool for guiding an interventional device towards the access site (shown in 840).

Illustration 802 shows interventional device 842 as being inserted into the vessel lumen, via the access site 800. Insertion of the interventional device 842 into the access site 800, the access site 800 diameter increases causing pulling and tensioning of the sutures 840. As this occurs, the resilient member in the tensioning tube 820 is compressed to maintain tension in the sutures 840 such that the vessel wall closes around the interventional device 842 ensuring that there is no extraneous bleeding around the interventional device 842.

When the interventional device 842 is removed from the access site 800, the resilient member in the tensioning tube 820 will expand, pulling the sutures 840 towards one another to close the access site 800 (illustrated in 803). An interventional device (either the same one or a different one) may then be reinserted into the access site using the process shown in 802.

When the procedure is complete and access to the vessel lumen is no longer desired, the access site 800 may be closed more permanently using suture lock 860. As described herein, suture lock 880 may be crimped or otherwise locked. Then the sutures may then be cut, releasing the tensioning tube 820 assembly. Thus, as shown in illustration 804, the anchors 850, distal ends of the sutures 840, and the suture lock 880 remain to keep the vascular opening closed. If a guidewire was used during the procedure, it can also be removed before locking the suture lock 860.

Each of the FIGs. and embodiments discussed below illustrate various ways to provide dynamic tensioning to sutures for closing access sites. These implementations permit installation of suture anchors and sutures with slack in the sutures, which can also permit installation of, for example, large sheaths and catheters into the access site without concern of cutting, severing. or breaking pre-tensioned sutures. Optionally, the embodiments described below allow for larger tensioning or cinching force to be applied on the sutures. Moreover, the sutures can be loosened any number of time for insertion or reinsertion of interventional devices in the access site without causing the sutures to break because of potential additional forces on the tensioned sutures. A larger tensioning force can also be applied because the sutures can be tensioned dynamically. The tension in the sutures can vary based on suture size, application, resilient member type, etc. As one example, about 1 to about 2 pounds of force can be applied on each suture. As another example, about 1.5 pounds of force can be applied on each suture. As previously noted, higher or lower forces may be applied based on a particular application of the disclosed embodiments. Each of the embodiments described below can be implemented in conjunction with previously described embodiments above.

Figure 10A:
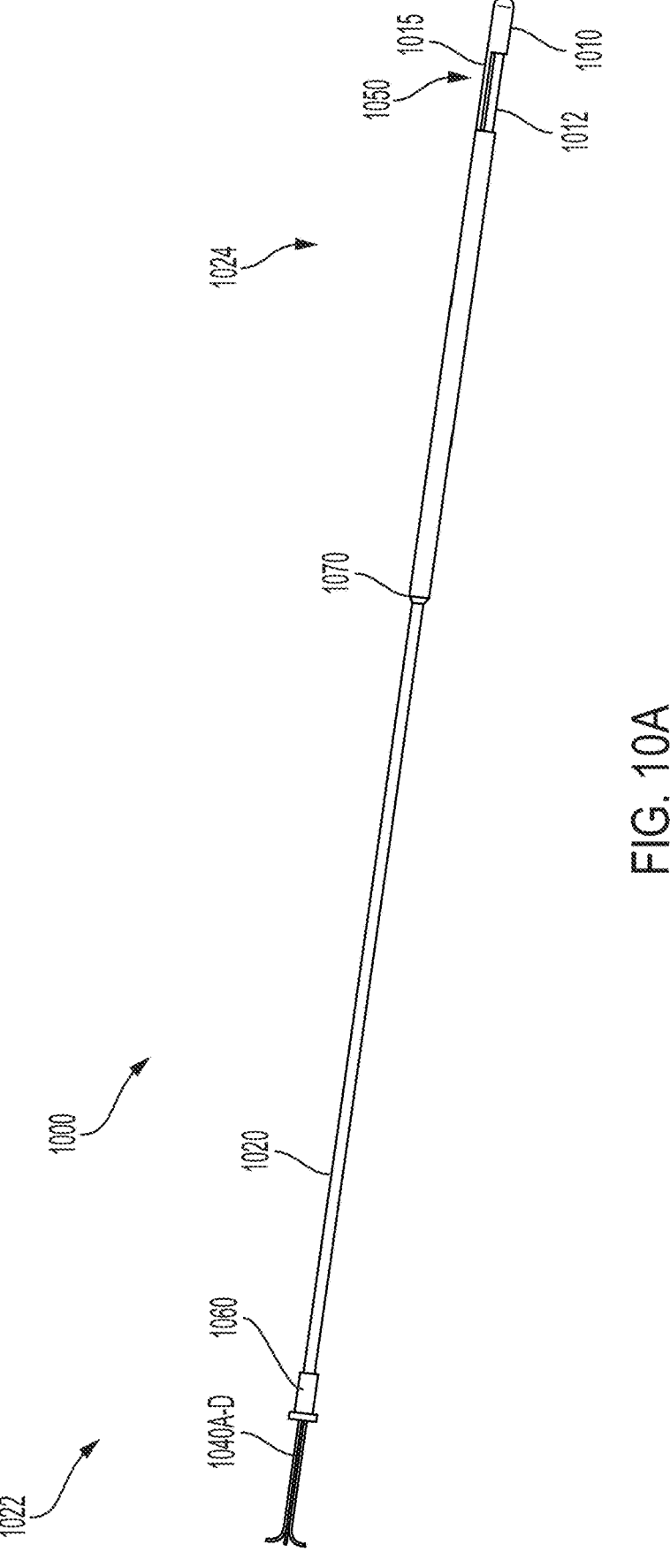
FIG. 10A is a perspective view of an alternative arrangement of an example dynamic vascular access and closure device.
Figures 10B, 10C:
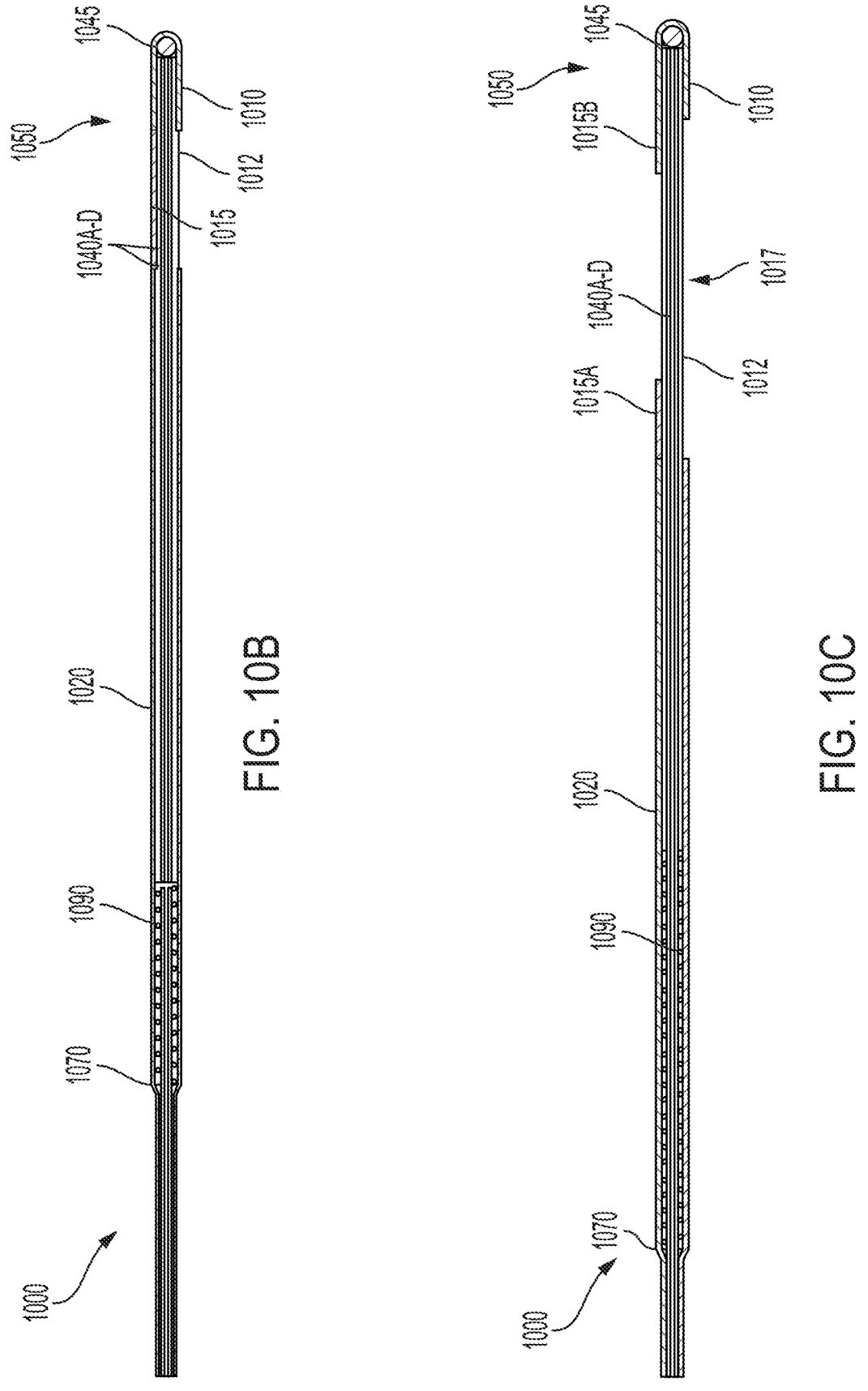
FIG. 10B is a cross sectional view of the example dynamic vascular access and closure device of FIG. 10A in a first position.
FIG. 10C is a cross section view of the example dynamic vascular access and closure device of FIG. 10A in a second position.

FIG. 10 is a perspective view of an alternative arrangement of an example dynamic vascular access and closure device. As shown in the FIGS. 10A, 10B, and 10C, the dynamic vascular access and closure device 1000 includes a tensioning tube 1020 having a distal end 1022 and a proximal end 1024. The distal end 1022 is the working end that is placed in proximity to a blood vessel. One or more suture filaments 1040A-D (also, interchangeably referred to as suture wires and sutures) extend axially through the tensioning tube 1020 between the distal end 1022 and the proximal end 1024, where a distal end of each suture wire is coupled to a suture anchor (not shown). A resilient member and a force applicator 1012 are at least partially disposed within the tensioning tube 1020.

As shown in the FIGs. and described above with respect to other embodiments (e.g., those shown and described with respect to FIGS. 1-5), the tensioning tube 1020 includes an elongate, hollow, tubular outer shaft which defines an inner lumen within which other components can extend through or be placed. While tensioning tube 1020 is illustrated as having a circular cross section, other cross sections, such as a square, rectangle, ellipse, etc. are also within the scope of this disclosure. The inner lumen can include a first section that has a smaller diameter compared to a second section. The smaller diameter of the first section is large enough to allow the suture wires 1040A-D to freely extend through it. The larger diameter of the second section is large enough to house the resilient member and the force applicator 1012.

In various implementations, tensioning tube 1020 can include a resilient member stop 1070. The resilient member stop 1070 can take a variety of forms, such as a step defined by a change in diameter of the tensioning tube from the larger lumen diameter to the smaller lumen diameter (as shown in FIG. 10), a gradual tapering of the tensioning tube 1020 from the larger lumen diameter to the smaller lumen diameter, a pin or other structure extending through the lumen orthogonal to the main axis of the tensioning tube 1020, or other suitable forms. As described above, tensioning tube 1020 may be made from a variety of materials, such as polymers (e.g., plastics, rubber, etc.), metals or alloys (e.g., titanium, stainless steel), or any other suitable material with sufficient stiffness to prevent deformation under the compressive load applied by the tensioned sutures 1040A-D.

A force applicator 1012 may be an inner biasing tube that is at least partially disposed within the inner lumen at the proximal end 1024 of the tensioning tube 1020 such that a distal end of the force applicator may reside inside the inner lumen while a proximal end lies outside the inner lumen. In various implementations, the force applicator 1012 may be a hollow tube. Force applicator 1012 may be freely moveable with respect to the tensioning tube 1020. While the force applicator 1012 is shown as having a circular cross section, other cross-sectional shapes can be used, such as a square, rectangle, ellipse, or others. The force applicator 1012 and the tensioning tube 1020 may have similar or different cross-sectional shapes. Force applicator 1012 may also be made from a variety of materials, such as plastics or metals, with sufficient stiffness to prevent deformation under the compressive load applied by the tensioned sutures 1040A-D.

As shown in FIGS. 10B-10C, a resilient member 1090 may be disposed within the tensioning tube 1020 between the resilient member stop 1070 and the distal end of the force applicator, as described in greater detail above. In various implementations, the resilient member 1090 may be a coiled wire such as a spring and/or other types of resilient members that can be compressed against the resilient member stop 1070. For example, the resilient member 1090 may be an elastic tube or other structure capable of being repeatedly compressed and decompressed upon application of an axial force on one or both of its ends such as, without limitation, an air spring, hydraulic/gas spring, motor, or any now or hereafter known resilient members. As an example, resilient member may be a linear actuator configured to tension sutures 1040A-D.

In various implementations, the force applicator 1012 can be held in a first position by a tension lock 1050. Example tension locks are described below in more detail and are configured to hold the force applicator 1012 in one or more positions with respect to tensioning tube 1020. For example, the tension lock 1050 can maintain the force application in the first position shown in FIG. 10B such that the resilient member is in a compressed state. By causing compression of the resilient member, slack can be achieved in the sutures 1040A-D. This initial slack in the sutures can have several advantages. The slack can permit large size sheaths to be placed into vessels between the sutures while reducing the risk of breaking or cutting the sutures. Once a large sheath has been inserted into the vessel, and tension on the sutures is desired (e.g., to close the access site), the tension lock can be manipulated (e.g, the bridge can be cut or otherwise broken) permitting the resilient member to expand causing movement of the force applicator 1012 in the proximal direction towards a second position and tensioning of the sutures. As described in greater detail below, tension lock 1050 can take various forms, such as a frangible bridge, suture bridge (also referred to as a trigger suture), reversible mechanical structure (such as a rotatable pin and slot combination). These variations are discussed in greater detail below with respect to FIGS. 11A-13B). The slack in the sutures should be enough to allow easy insertion of large sheath sizes. In some embodiments, the amount can be a suture length that is at least about half of the circumference of the sheath to about 3 inches. Other embodiments can include slack corresponding to a suture length of about 1 inch to about 4 inches.

In the specific example, of FIGS. 10B, 10C, 11A and 11B, tension lock 1050 comprises an end cap 1010 coupled to a proximal end of the force application 1012 and a frangible bridge 1015 portion extending distally from the end cap 1010 and coupled to a proximal end of the tensioning tube 1020. Optionally, a suture knot 1045 or similar connection can be made to hold or otherwise couple the proximal ends of sutures 1040A-D within end cap 1010 such that movement of the end cap in the proximal end causes tensioning of the sutures. The frangible bridge can be made of a suitable polymer, metal, or other suitable material. During installation of the suture anchors and initial access of the site (e.g., to install a sheath), the dynamic vascular access and closure device 1000 is configured to be in a first state in which the tension lock is configured to hold the resilient member in a compressed state, causing slack in the sutures. Specifically, when the bridge 1015 is intact it is configured to hold the force applicator in a first position that causes compression of the resilient spring (illustrated in FIGS. 10B and 11A) and shortening of the suture length held within the tensioning tube (thereby causing slack in the sutures around the access site).

Figures 11A, 11B:
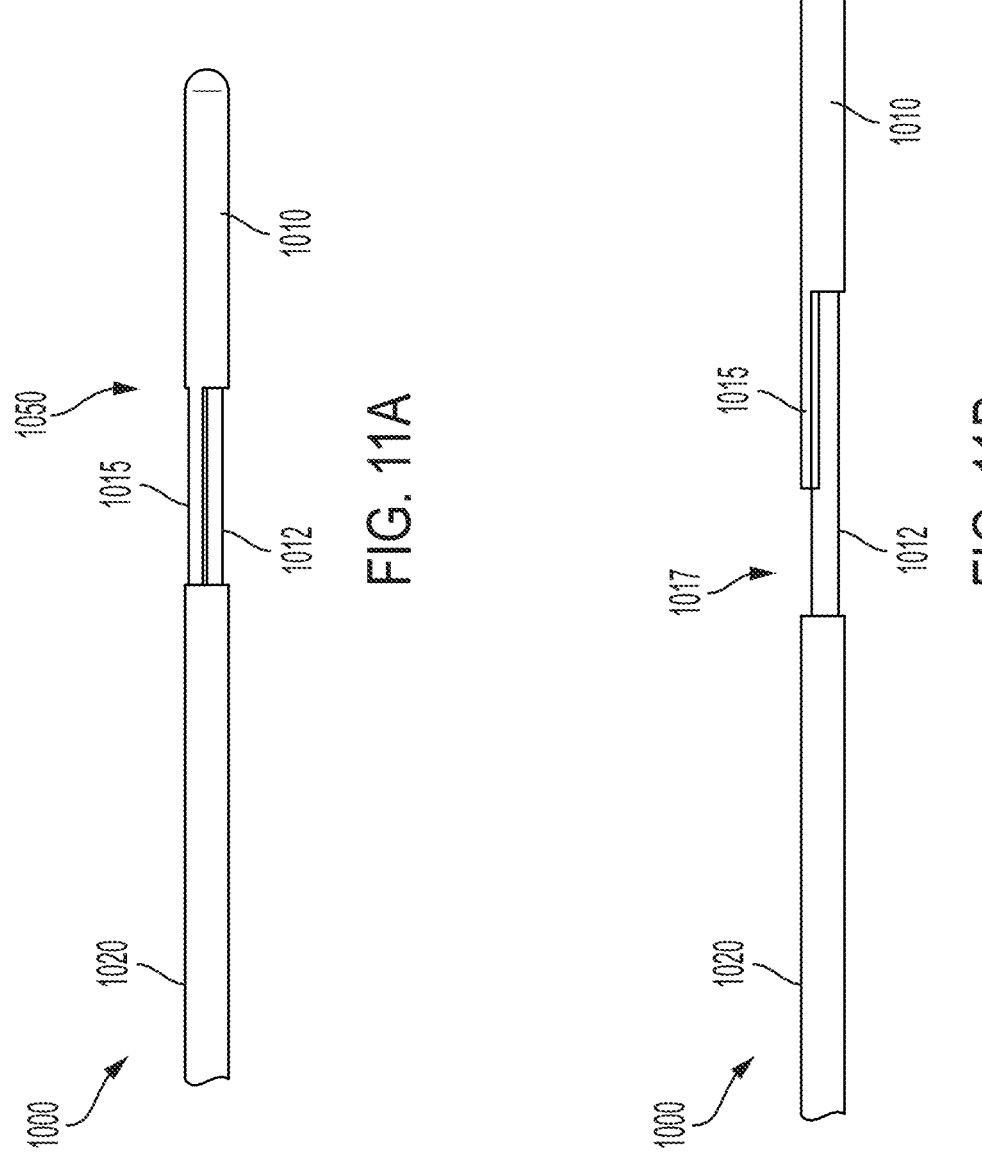
FIG. 11A is an enlarged view of a proximal end of the example dynamic vascular access and closure device of FIG. 10 in the first position.
FIG. 11B is an enlarged view of a proximal end of the example dynamic vascular access and closure device of FIG. 10 in the second position.

When the user is ready to tension the sutures, the bridge 1015 may be broken, as illustrated in FIGS. 10C and 11B such that the dynamic vascular access and closure device 1000 is configured to be in a second state in which the sutures anchored around the access site are tensioned. When the bridge 1015 is broken, the force applicator is not constrained to its first position such that the compression within the resilient member is released and the force applicator moves to a second position (illustrated in FIGS. 10C and 11B). Specifically, when the bridge is broken, the compressed resilient member is allowed to at least partially expand such that spring force stored in the compressed spring causes movement of the end cap of the tension lock (and the force applicator) to a second position (shown in FIGS. 10C and 11B) which in turn causes tensioning of the anchored sutures (because of pulling of the proximal ends of the sutures in a proximate direction). The tension is visible in FIGS. 10C and 11B from the movement of end cap 1010 and force application 1012 through the creation of gap 1017. In some embodiments, the bridge 1015 can be broken in multiple pieces 1050A, 1050B. In this example, the bridge can be broken by cutting (e.g., with a knife, scissors, scalpel, or other blade), by snapping or twisting (e.g., by hand or with a tool such as hemostats). In various embodiments, the bridge can be broken manually (for example, direct cutting with scalpel) or automatically (for example, by a machine or electronically or by the user pushing a button that causes the bridge to be broken).

Figure 12A:
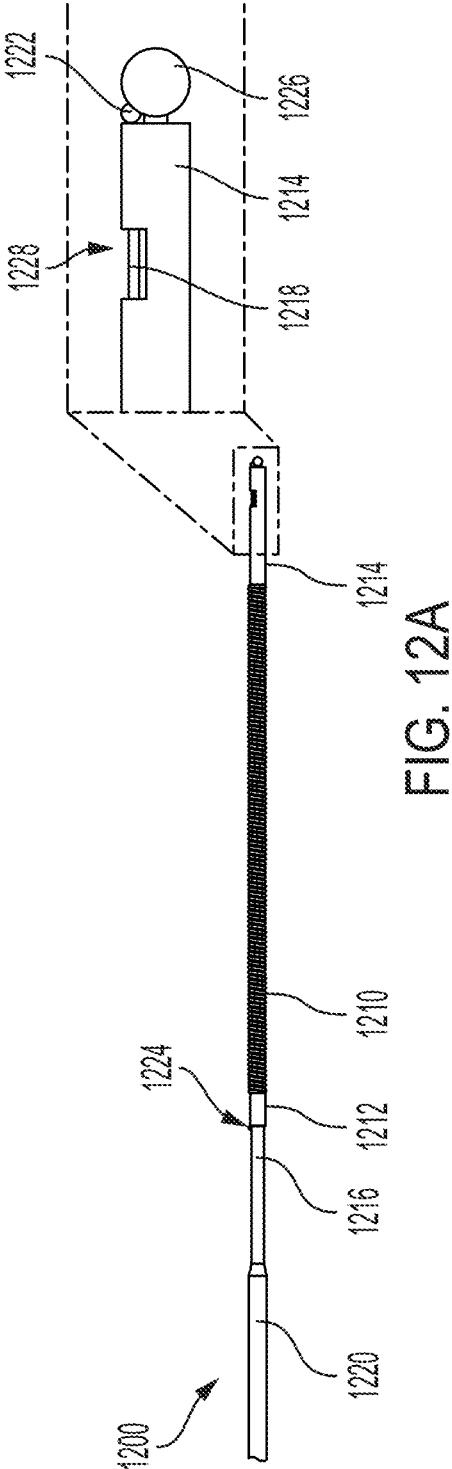
FIG. 12A is a side view of an alternative arrangement of an example dynamic vascular access and closure device in a first position.
Figure 12B:
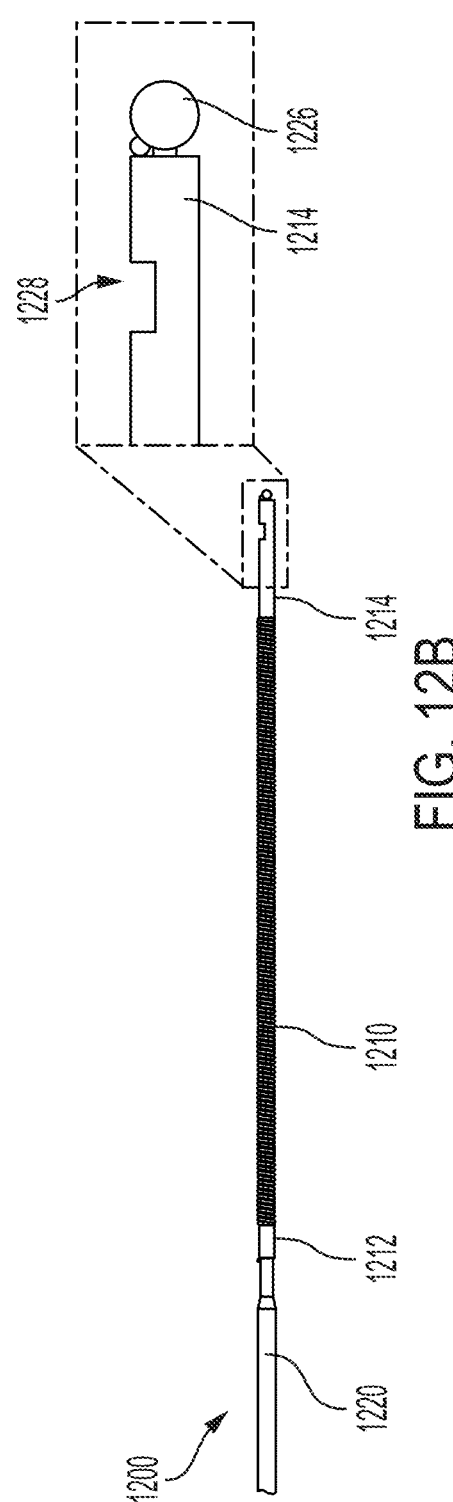
FIG. 12B is a side view of an alternative arrangement of the example dynamic vascular access and closure device of FIG. 12A in a second position.
Figure 12C:
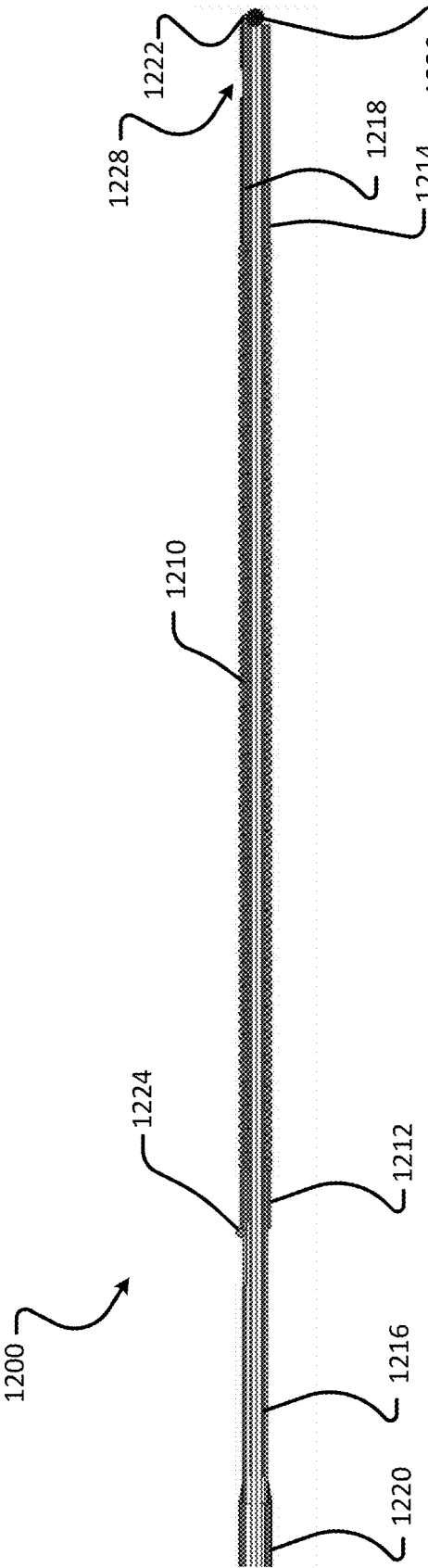
FIG. 12C is a cross sectional view of a portion of the example dynamic vascular access and closure device of FIG. 12A.

FIG. 12A is a side view of an alternative arrangement of an example dynamic vascular access and closure device 1200 in a first state, while FIG. 12B shows the device in a second state. In this embodiment, an external resilient member 1210 (illustrated as a compression spring) has a distal end cap 1212 and a proximal end cap 1214. The resilient spring 1210 is mounted over a smaller diameter section 1216 of a tensioning tube 1220 because mounting the resilient member 1210 permits the use of larger springs as the resilient member 1210. The remainder of the tensioning tube assembly can remain the same, while the size of the resilient member 1210 (and thus the resulting cinching force) can be adjusted. In some embodiments, the distal larger diameter section of tensioning tube 1220 can be made from an axially flexible material, such as a polymer to provide flexibility around the access site without concerns of twisting or buckling a stiff metal tube. Conversely the smaller diameter proximal portion 1216 can be made from a more rigid material, such as a metal like stainless steel, with more rigidity. One or more sutures extend between a distal end and a proximal end of the tensioning tube and may exit the proximal end to form a suture knot 1226. The suture knot 1226 may be formed outside of the proximal end of the proximal end cap 1214 such that compression/expansion of the spring causes movement of the suture knots for tensioning or slackening of the sutures. An optional sheath may cover the resilient spring and/or other components of the device shown in FIGS. 12A and 12B (not shown here). While the dynamic vascular access and closure device 1200 of FIGS. 12A and 12B includes an external spring design, the disclosure is not so limiting, and a similar tension lock can be used with other embodiments of this disclosure. Similarly, the above-described tensioning lock can be used with the external spring configuration of the dynamic vascular access and closure device.

A tension lock 1218 in the form of a trigger suture extends from distal end cap 1212 to proximal end cap 1214 (i.e., from knot or stop 1222 to 1224). The tension lock 1218 holds resilient member 1210 in a compressed position. The length of the suture of tension lock 1218 will control the amount of compression experienced by resilient member 1210 (i.e., a shorter suture will cause more compression and more slack, while a longer suture will cause less compression and result in less slack in the sutures for closing the access hole (illustrated by suture knot or stop 1226)). During installation of the suture anchors and initial access of the site (e.g., to install a sheath), the dynamic vascular access and closure device 1200 can be held in a first state (as illustrated by FIG. 12A) in which the tension lock is configured to hold the resilient member in a compressed state, causing shortening of the suture length within the tensioning tube and, hence, slack in the sutures near the vascular access site.

Proximal end cap 1214 can include a window 1228, which exposes a portion of tension lock suture 1218. Accordingly, when a user wishes to release the tension lock 1218 and tension the access site sutures, tension lock suture 1218 can be cut or otherwise broken through window 1228, as illustrated in FIG. 12B. When the suture is cut or broken, the compressed resilient member is allowed to at least partially expand such that spring force stored in the compressed spring causes movement of the proximal end cap 1214 to the second position (shown in FIG. 12B) along with the suture knot 1226. As, the length of the sutures within the tensioning tube increases which in turn causes tensioning of the anchored sutures around the access site. The tension is visible in FIG. 12B from the elongation of resilient member 1210 and the less visible amount of ten (as compared to FIG. 12A). As described above, the bridge could be broken by cutting (e.g., with a knife, scissors, scalpel, or other blade), by snapping or twisting (e.g., by hand or with a tool such as hemostats). In various embodiments, the bridge can be broken manually (for example, direct cutting with scalpel) or automatically (for example, by a machine or electronically or by the user pushing a button that causes the bridge to be broken).

Figures 13A, 13B:
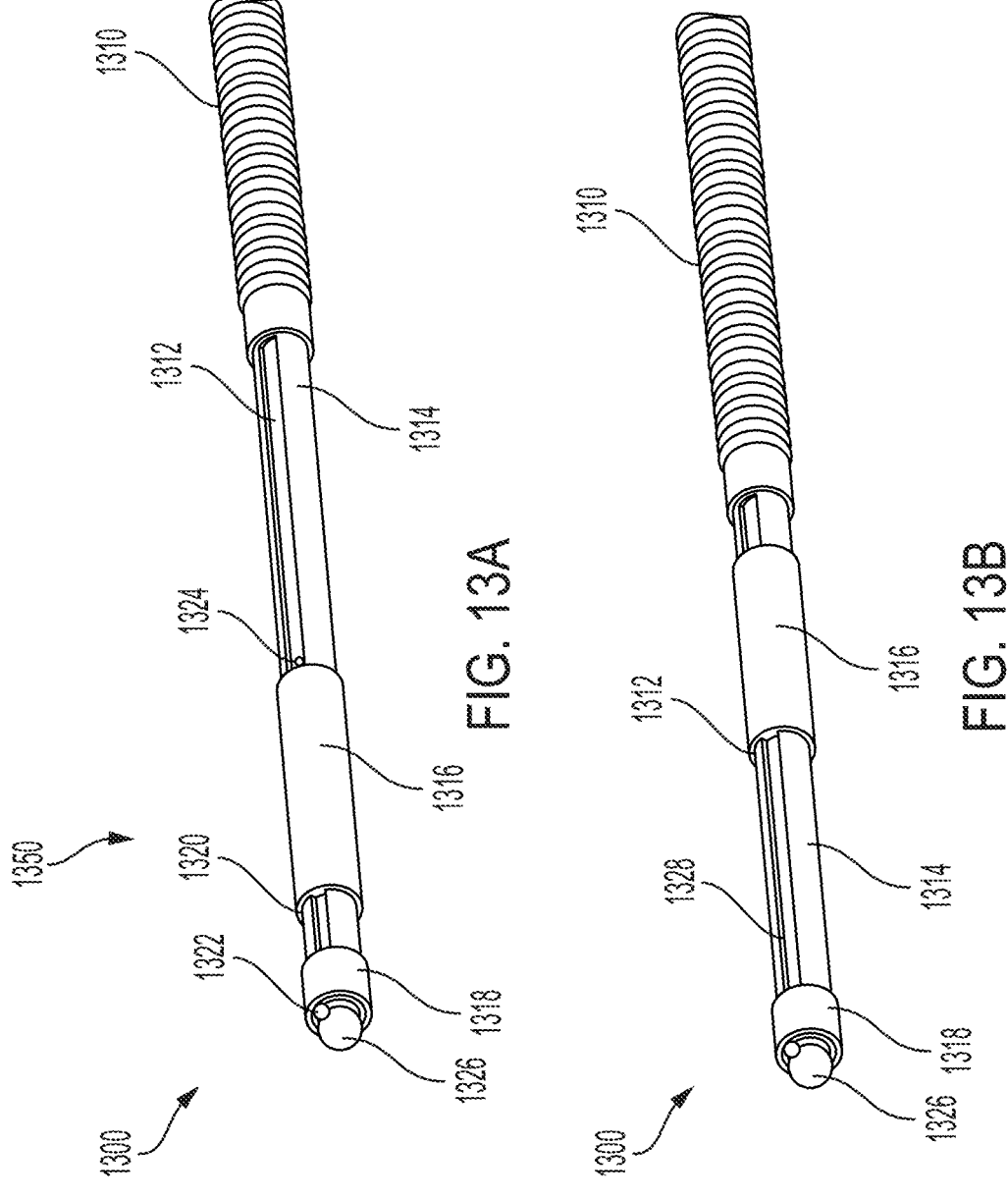
FIG. 13A is a perspective view of an alternative arrangement of an example dynamic vascular access and closure device in a first position.
FIG. 13B is a perspective view of the example dynamic vascular access and closure device of FIG. 13A in a second position.

FIG. 13A is a perspective view of an alternative arrangement of an example dynamic vascular access and closure device 1300 in a first state. FIG. 13B is a perspective view of an alternative arrangement of an example dynamic vascular access and closure device in a second state. Dynamic vascular access and closure device 1300 includes an external resilient member design similar to dynamic vascular access and closure device 1200 of FIGS. 12A-12B. However, the tension lock can be used with any of the embodiments of this disclosure.

In this example, resilient member 1310 is placed around the tensioning tube (not shown here). Furthermore, the tension lock 1350 comprises an inner tube 1312 coupled to the distal end of resilient member 1310. Control tube segment 1316 is slidably disposed around outer 1314. Control tube segment 1316 is also rigidly connected to inner tube 1312. Accordingly, outer tube 1314 acts a rail for sliding movement of control tube segment 1316. Because control tube segment 1316 is fixed to the proximal end of resilient member 1310, as control tube segment 1316 moves in a proximal direction (i.e., away from the access site and toward end cap 1318), resilient member 1310 is compressed. This compression results in slack in the sutures. Specifically, when the control tube segment moves in a proximal direction, the tensioning tube is effectively shortened and the amount of suture held within the tensioning tube is reduced. The shortening of the suture length held within the tensioning tube causes slack in the sutures around the access site. Conversely, as control tube segment 1316 moves distally (i.e., toward from the access site and away from end cap 1318), resilient member 1310 can expand and cause tension in the sutures that are closing the access site. The sutures 1328 are disposed within inner tube and can have a knot or stop 1326 at their proximal end that can contact end cap 1318. End cap 1318 can be fixed around the proximal end of outer tube 1314.

A suture bridge tension lock 1320 can hold control tube segment 1316 in a first retracted position. For example, the tension lock 1320 in the form of a trigger suture extends from end cap 1318 to the proximal end of control tube segment 1316 (i.e., from knot or stop 1322 to 1324). Accordingly, during installation of the suture anchors and initial access of the site (e.g., to install a sheath), the dynamic vascular access and closure device 1300 can be held in a first position (as illustrated by FIG. 13A) in which the tension lock 1320 is configured to hold the resilient member 1310 in a compressed state, causing slack in the sutures. The length of the suture of tension lock 1320 will control the amount of compression experienced by resilient member 1310 (i.e., a shorter suture will cause more compression and more slack, while a longer suture will cause less compression and result in less slack in the sutures 1328.

When a user wishes to release the tension lock 1320 and tension the access site sutures, tension lock suture 1320 can be cut or otherwise broken, for example at the exposed segment between end cap 1318 and control tube segment 1316. When the user is ready to tension the sutures, the bridge is broken, as illustrated in FIG. 13B. When the bridge is broken, the compressed resilient member is allowed to at least partially expand such that the suture knot moves proximall causing an increase in the length of the sutures within the tension tube and tension in the anchored sutures around the access site. The tension is visible in FIG. 13B from the distal movement of control tube segment 1316 (away from end cap 1318). If the user wishes to release the tension on sutures 1328, the user only needs to pull control tube segment 1316 in the proximal direction toward the end cap 1318 causing compression of the resilient spring and shortening of the length of the sutures within the tensioning tube causing slack in the anchored suture around the access site. Accordingly, device 1300 provides the additional advantage of easily being able to add slack to the sutures after the initial installation.

Figures 14A, 14B, 14C:
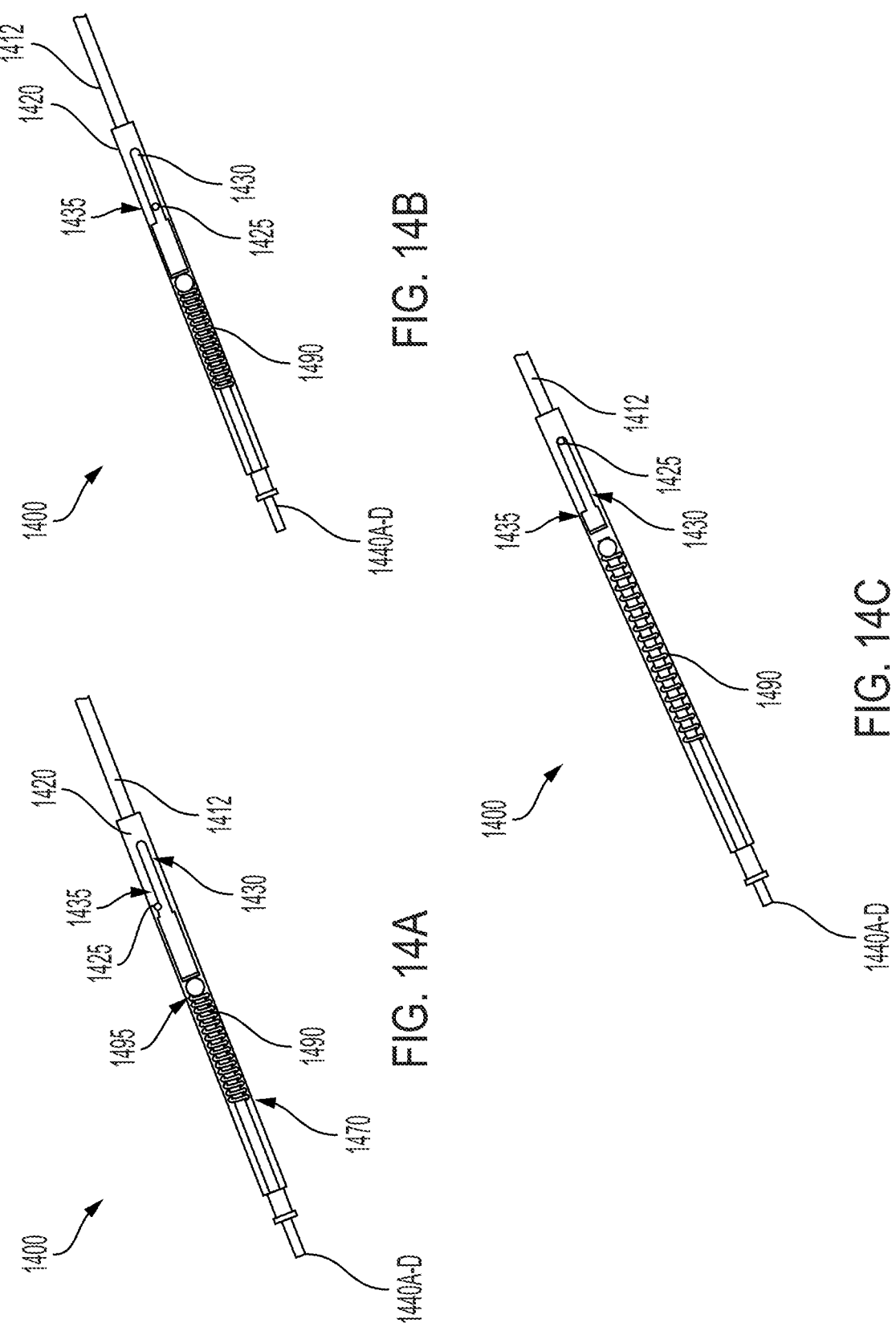
FIG. 14A is a perspective view of an alternative arrangement of an example dynamic vascular access and closure device in a first position.
FIG. 14B is a perspective view of the example dynamic vascular access and closure device of FIG. 14A in a second position.
FIG. 14C is a perspective view of the example dynamic vascular access and closure device of FIG. 14A in a third position.

FIG. 14A is a perspective view of an alternative arrangement of an example dynamic vascular access and closure device 1400 in a first state. FIG. 14B is a perspective view of the example dynamic vascular access and closure device 1400 in a second state. FIG. 14C is a perspective view of the example dynamic vascular access and closure device of 1400 in a third state. Dynamic vascular access and closure device 1400 includes an easily reversible tensioning system using a pin and slot. Dynamic vascular access and closure device 1400 includes a tensioning tube 1420 and force application 1412. Disposed within tensioning tube 1420 is resilient member 1490, which can contact resilient member stop 1470. Running axially through tensioning tube 1420 are sutures 1440A-D, which can terminate the proximal end 1495 of resilient member 1490. In other embodiments, the proximal ends of sutures 1440A-D could be attached to force applicator 1412. Tensioning tube 1420 includes a slot or recess 1430 running axially along its length at or near its proximal end. The slot 1430 can be sized and shaped to receive a pin 1425 or protrusion extending from force applicator 1412. At the distal end of slot 1430, tensioning tube 1420 can include a pin stop or catch 1435, which can be a flat or recessed region configured to hold pin 1425. In a first position, illustrated by FIG. 14A, pin stop 1435 holds pin 1425. In this position, force applicator 1412 is held by pin 1425 in distally forward position that compresses resilient member 1490, causing slack in sutures 1440A-D. When a user needs to tension sutures 1440A-D, the user can place the device 1400 and the tension lock mechanism in a second position rotate force applicator 1412 until pin 1425 is aligned with slot 1430, as illustrated by FIG. 14B. Resilient member 1490 can then expand as pin 1425 slides along slot 1430, tensioning sutures 1440A-D until pin 1425 reaches the proximal end of slot 1430. The resulting third position is illustrated by FIG. 14C. This easy-to-use rotating and sliding pin mechanism permits a user to add slack back to the sutures 1440A-D simply by pushing on the proximal end of force applicator 1412 until pin 1425 clears slot 1430, then rotating force applicator 1412 until it clears the slot. This movement will place the device back in the first position (illustrated by FIG. 14A), an permit slack to be held in the sutures by the device, without requiring the user to hold a portion of the device (i.e., by continually manually compressing the resilient member).

While some of the embodiments described above include different tensioning mechanisms (for example, an external spring vs. an internal spring design), either of the tensioning mechanisms can be configured to work with the various disclosed suture tension locks.

Figure 15A:
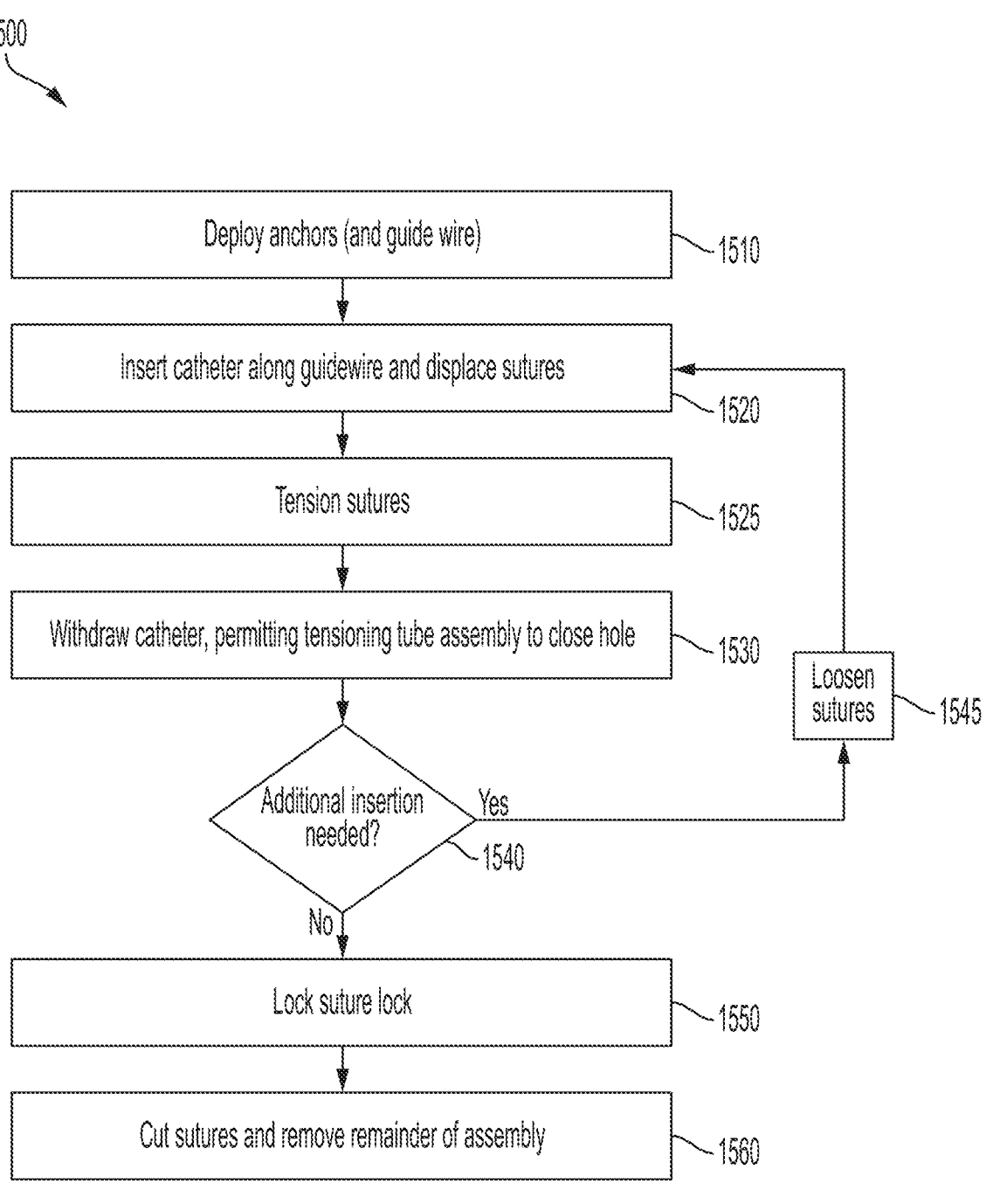
FIG. 15A is a flowchart illustrating another example method of using a dynamic vascular access and closure device.
Figure 15B:
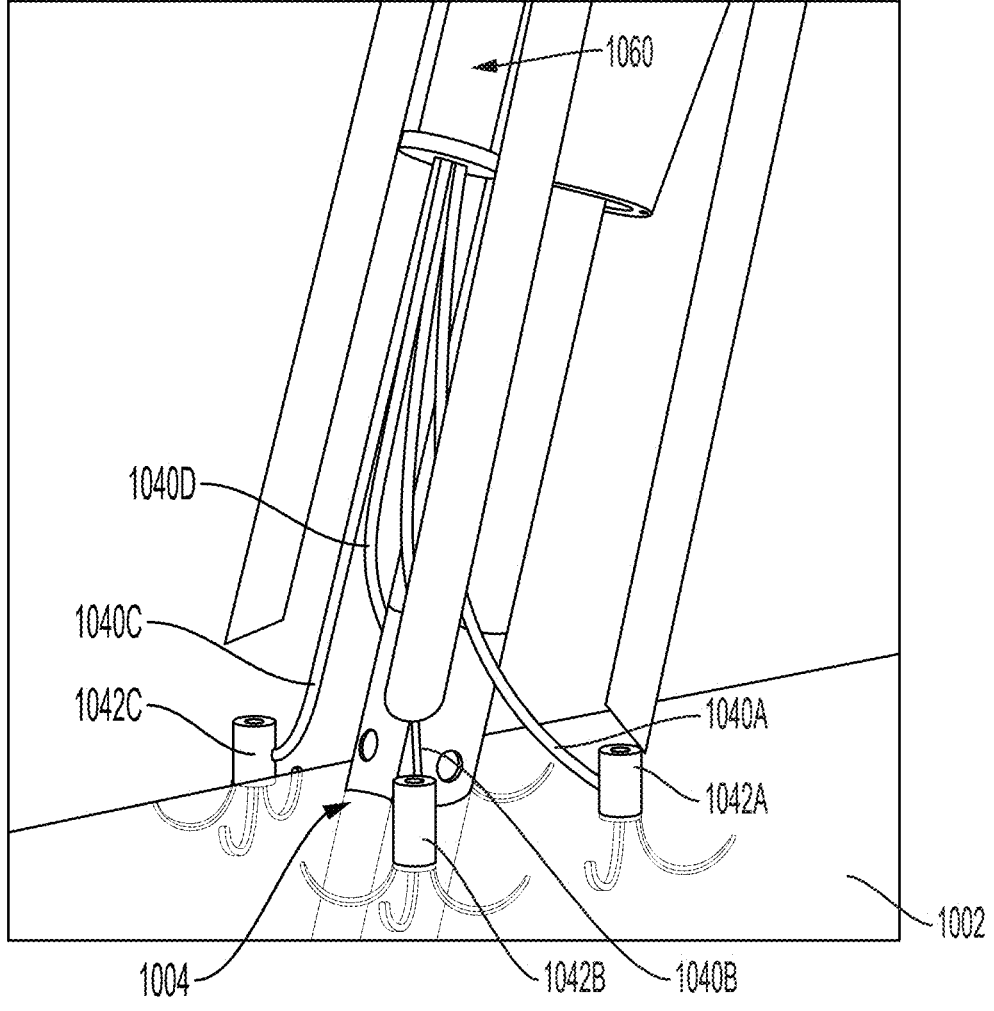
FIG. 15B is a schematic illustration of a portion of the example method of FIG. 15A.
Figure 15C:
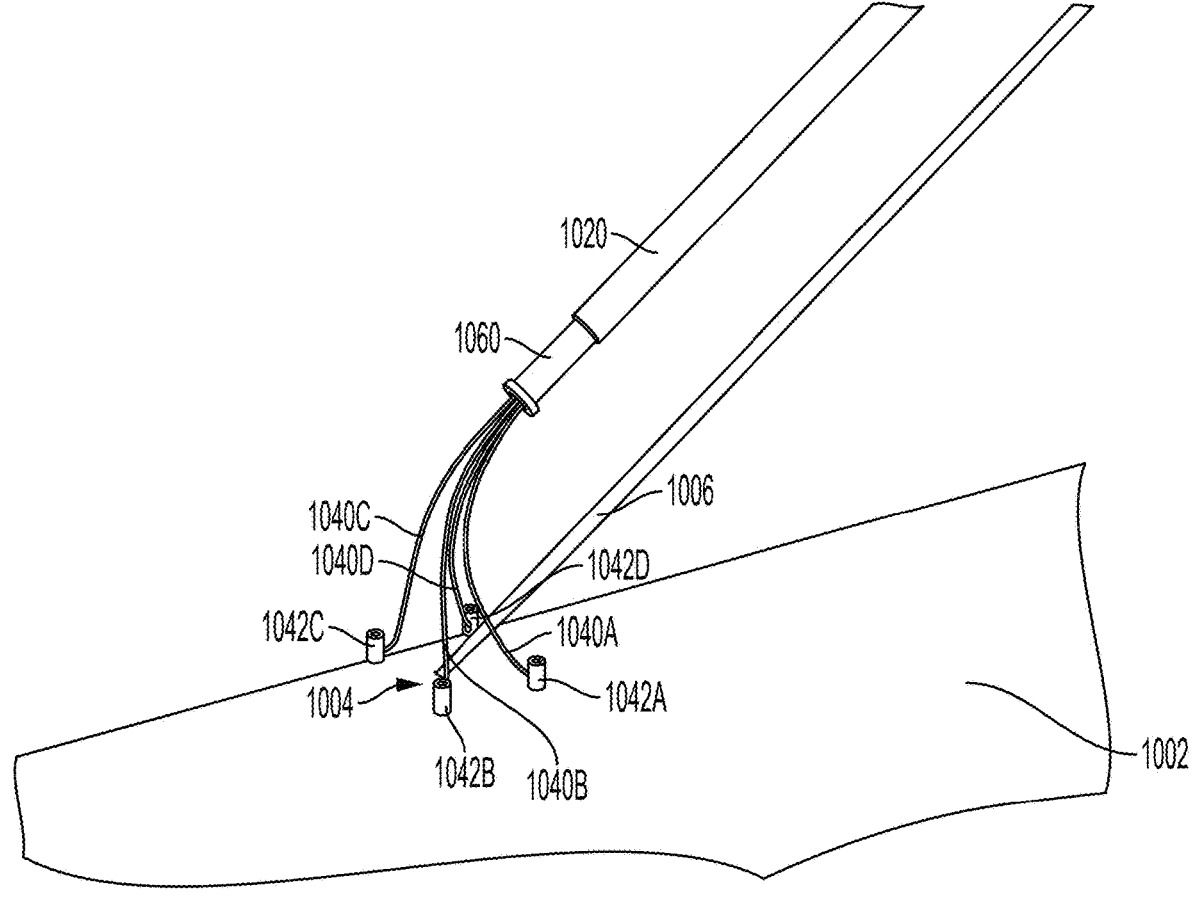
FIG. 15C is a schematic illustration of a portion of the example method of FIG. 15A.
Figure 15D:
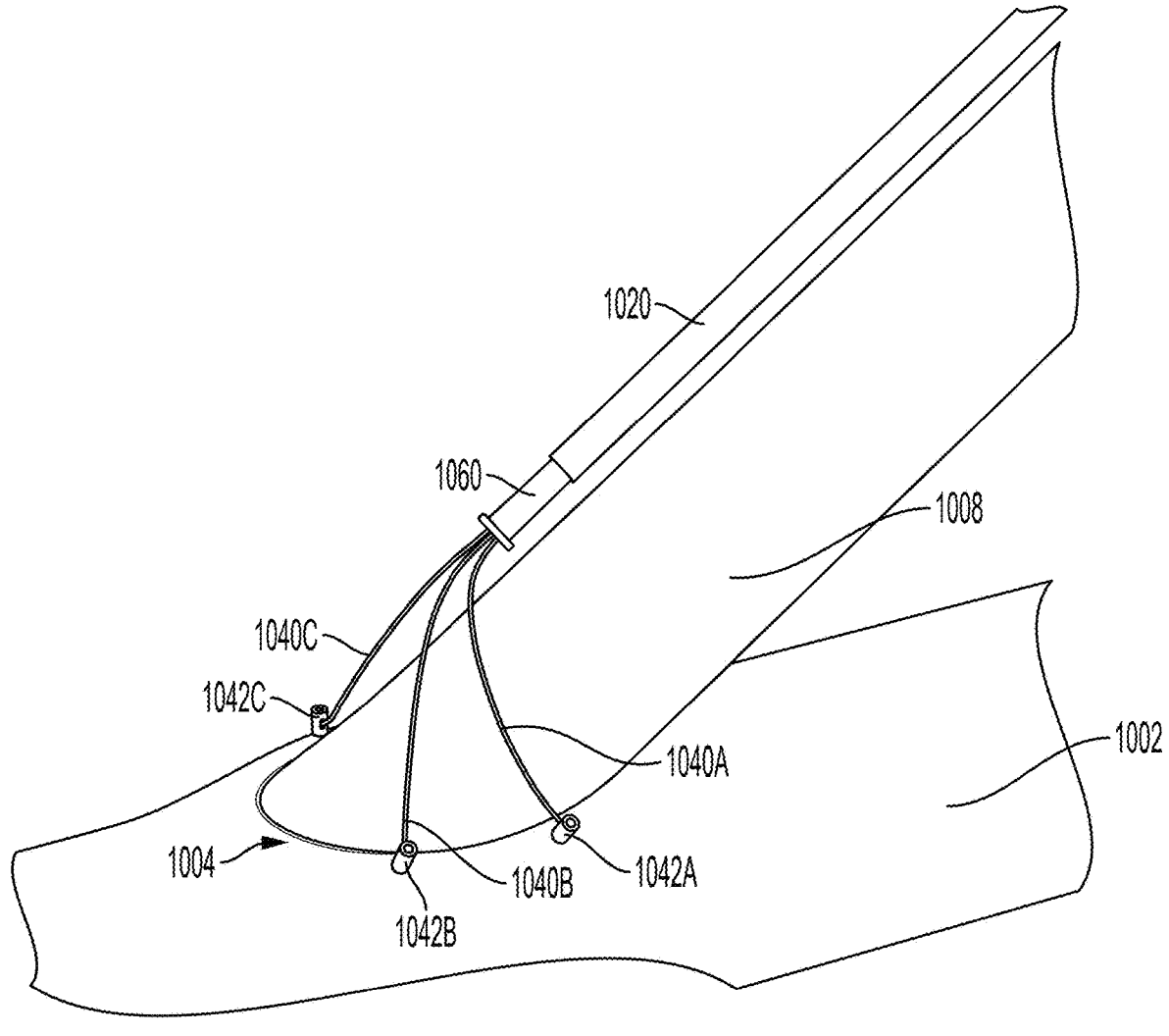
FIG. 15D is a schematic n illustration of a portion of the example method of FIG. 15A.

FIG. 15A is a flowchart depicting an example method 1500 for using a dynamic vascular access and closure device 1000, 1200, 1300, 1400 of this disclosure. Further, FIGS. 15B-15H illustrate various steps of method 1500 using a dynamic vascular access and closure device 1000, but method 1500 can be implemented using the various devices described above. At step 1510, the anchors and/or sutures may be deployed into the vessel wall using any now or hereafter known deployment devices. Step 1510 may also include deploying of a guide wire. At this step, the dynamic vascular access and closure device can tension the sutures around the guidewire and/or an access site or hole in the vessel. FIG. 15B is an illustration of step 1510, which shows suture anchors 1042A-D after being deployed by deployment tubes in a vessel 1002 around an access site 1004. FIG. 15C illustrates the sutures 1040A-D in a slacked position after being installed, along with guide wire 1006. The sutures extend through tensioning tube 1020.

At step 1520, method 1500 may include inserting an interventional device (such as a sheath) over the guide wire into the vessel. In other embodiments, the sutures and tensioning device could be deployed before a vascular access. Accordingly, the anchors may be placed without a guidewire and the guidewire can be inserted after the placement of the device. As described herein, when the interventional device is inserted, the suture may be displaced or pulled, permitting the access site in the vessel to expand. The force applied to the sutures by the interventional device can cause a compression (or, in applicable embodiments, extension) of the resilient member within the tensioning tube. The force applied by the resilient member to the sutures will hold the anchors close to the instrument, sealing the vessel wall around the periphery of the instrument and preventing or reducing any unwanted bleeding. In other embodiments, such as that illustrated by FIG. 15D, the sutures 1040A-D can have slack before and during the insertion of the interventional device 1008. As described above, this can permit the interventional device 1008 to be installed without risking cutting or otherwise breaking the sutures 1040A-D. With slack in the sutures 1040A-D, the access site 1004 can be permitted to expand to accept the interventional device 1008 into vessel 1002.

Figure 15E:
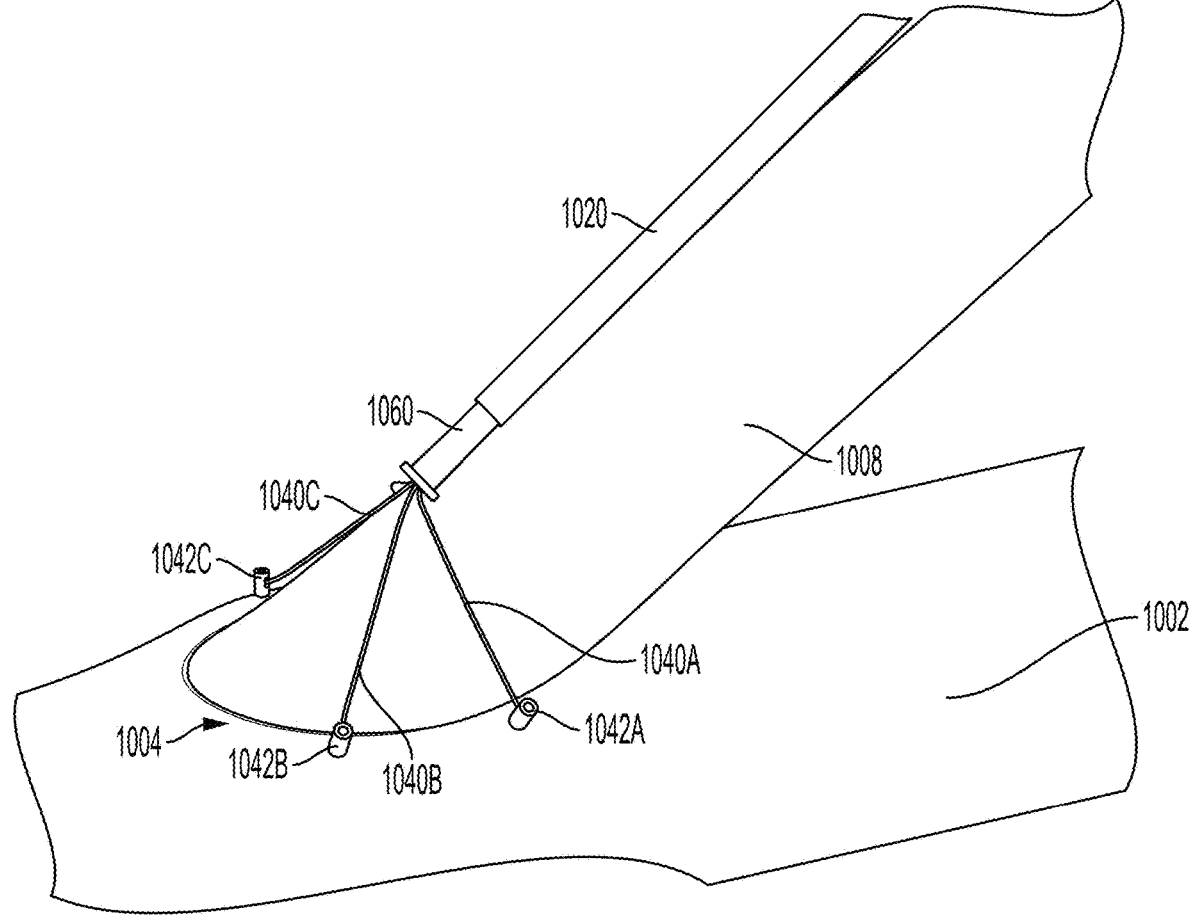
FIG. 15E is a schematic illustration of a portion of the example method of FIG. 15A.

At step 1525, method 1500 may include tensioning the sutures, for example by releasing a tension lock as described above with respect to any of dynamic vascular access and closure devices 1000, 1200, 1300, 1400. FIG. 15E illustrates tensioned sutures 1040A-D, closing the access site 1004 around interventional device 1008.

Figure 15F:
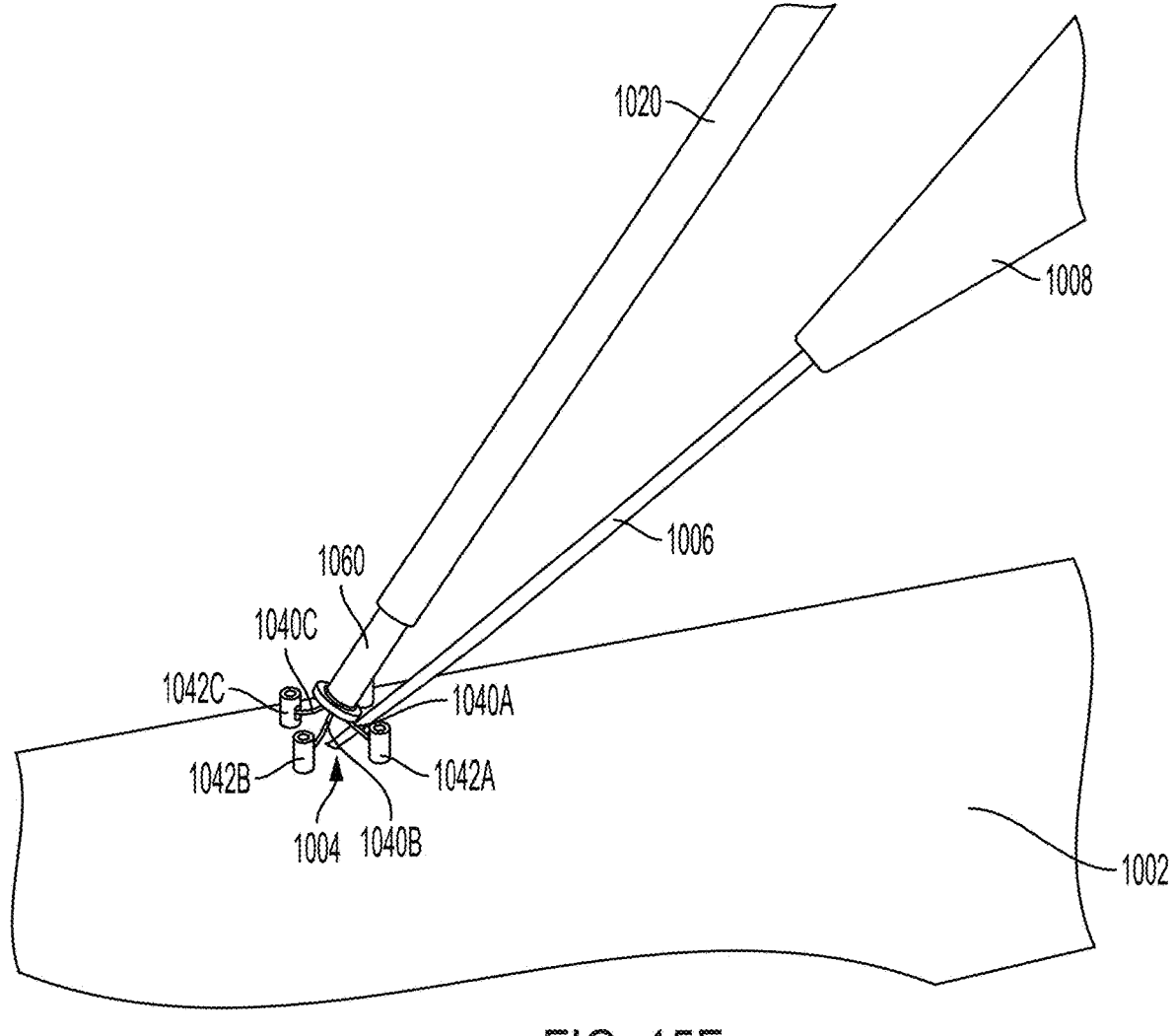
FIG. 15F is a schematic illustration of a portion of the example method of FIG. 15A.

At step 1530, the interventional device may be withdrawn from the vessel. As the instrument is withdrawn, the access hole will be closed by the sutures automatically as the resilient member is decompressed, which in turn can push on the suture stops and cause the sutures to cinch together. This automated closure of the access site can prevent bleeding when the interventional device is removed from the vessel. Such automated bleeding prevention is a significant improvement over the existing techniques because a user is not required to manually pinch the vessel to prevent the bleeding. Other times, a physician may need to employ a cross-over balloon, which can be balloon inserted from another access site and inflated temporarily to stop bleeding. The automated cinching provided by disclosed embodiments may mitigate the need for such a technique. Accordingly, through use of the dynamic vascular access and closure device, the procedure is made both easier for the surgeon and safer for the patient. Step 1530 is illustrated by FIG. 15F, which has interventional device 1008 being removed along guidewire 1006. As shown, the tension on sutures 1040A-D causes access site 1002 to close tightly around guidewire 1006.

Figure 15G:
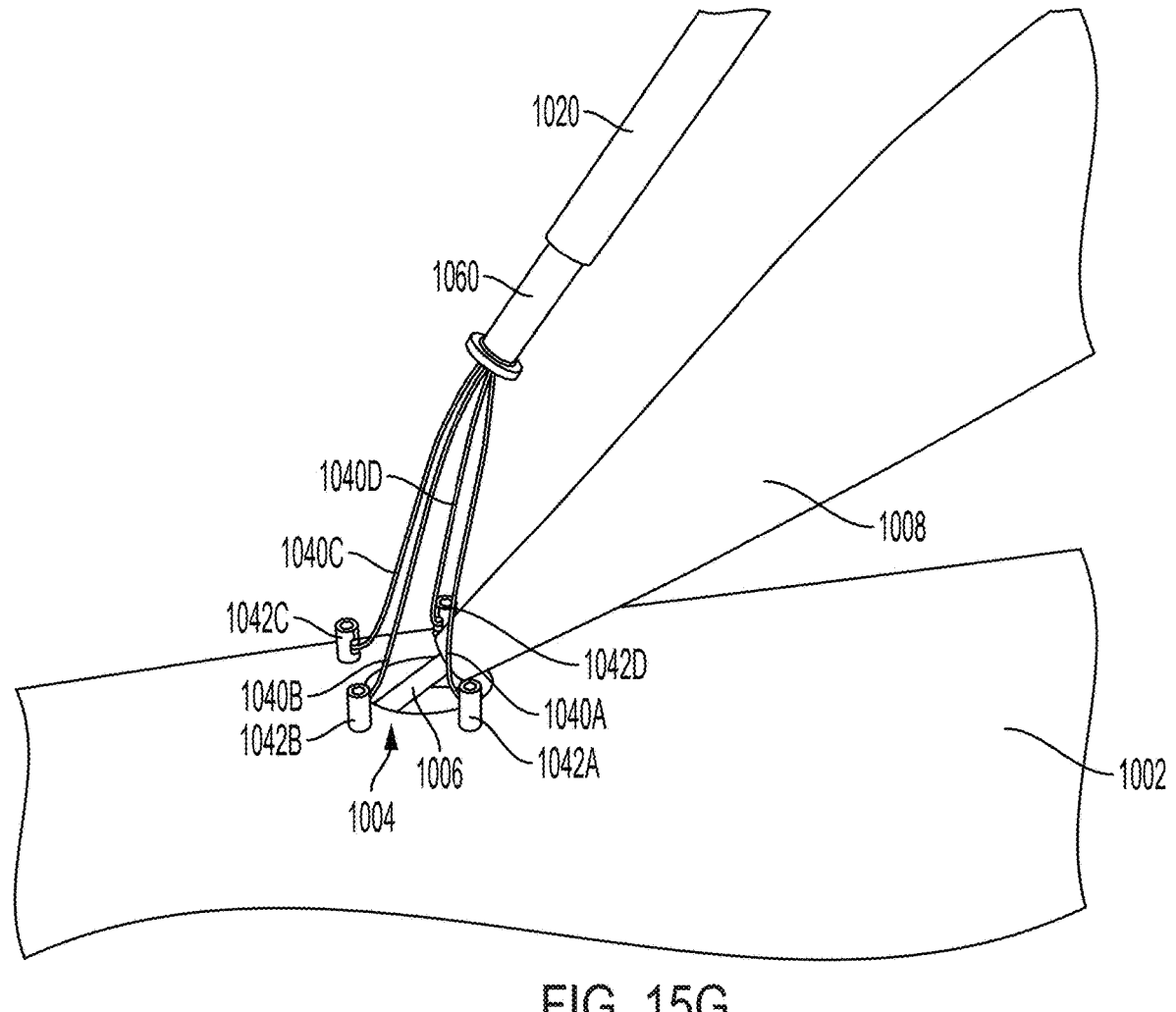
FIG. 15G is a schematic illustration of a portion of the example method of FIG. 15A.

As described herein, the dynamic vascular access and closure device 1000, 1200, 1300, 1400 of the disclosure also allows for reinsertion of an interventional device through the same access site. Accordingly, method 1500 may include a determination at step 1540 of whether an additional interventional device insertion is needed. If an additional interventional device insertion is needed, method 1500 may include step 1545 of loosening the sutures (for example, to prevent cutting or breaking of the sutures when the additional device is inserted). Loosening the sutures at step 1545 can include providing slack to the sutures by, for example, manually compressing the resilient member (or other methods disclosed above). After loosening the sutures, step 1520 may be repeated. FIG. 15G illustrates loosened sutures 1040A-D, permitting access site 1006 to expand to accept interventional device 1008 to be inserted into vessel 1002.

Figure 15H:
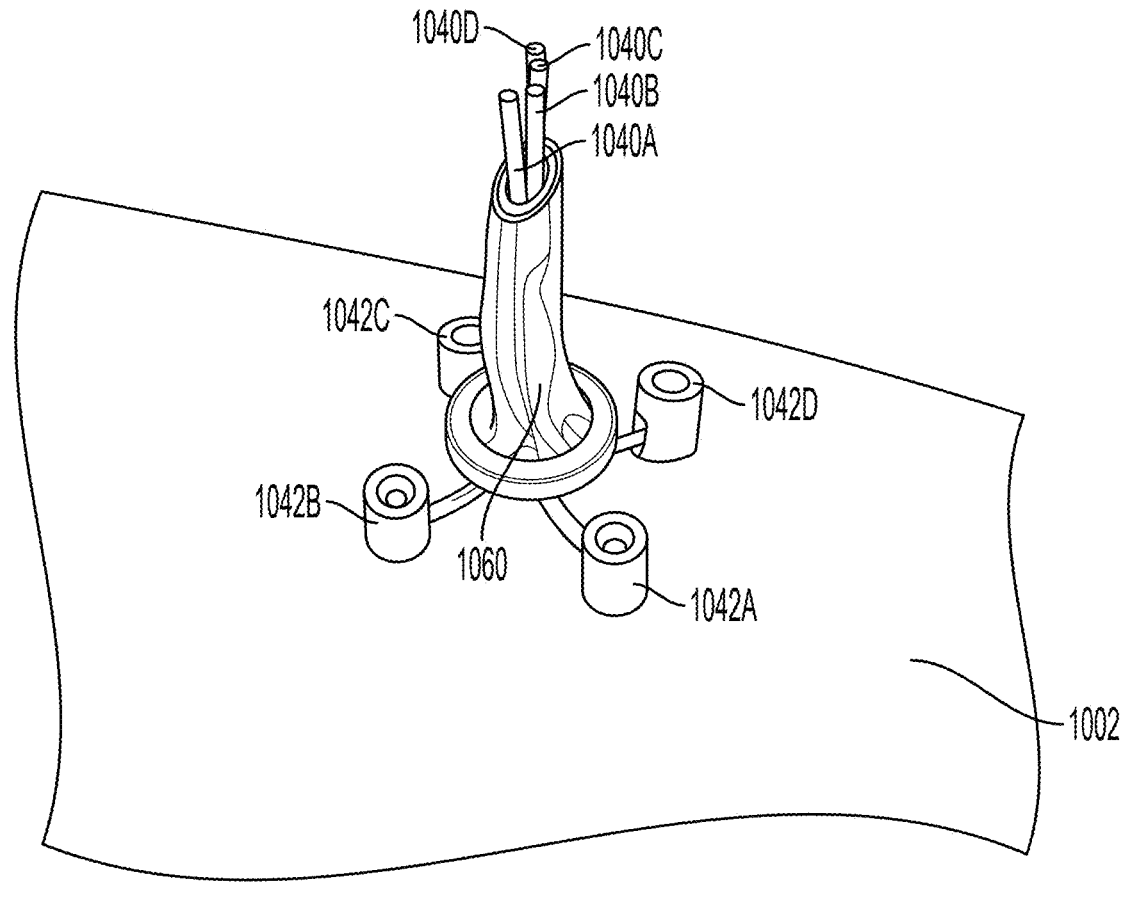
FIG. 15H is a schematic illustration of a portion of the example method of FIG. 15A.

If an addition interventional device insertion is not needed, step 1550 may be executed. At step 1550, the suture lock can be locked. As described herein, the suture lock may be locked by crimping a ferrule or locking a selectable lock, among other ways. At step 1560, the sutures may be cut. The sutures maybe cut at any desired position, such as the distal end of the tensioning tube between the tensioning tube and the suture lock, leaving a relative minimum amount of extra suture attached to the patient's vessel. The tensioning tube assembly may be removed thereafter. FIG. 15H illustrates a locked suture lock 1060 around sutures 1040A-D. In this example, suture lock 1060 is a ferrule which is crimped around sutures 1040A-D, which have been cut. In other embodiments, the suture could be cut at the proximal end of the resilient member, between the resilient member and the suture stop leaving a longer length of extra suture protruding from the suture lock (which may be used to tie a knot at the end of the suture lock to provide additional safety against unraveling of the sutures).

Figure 16:
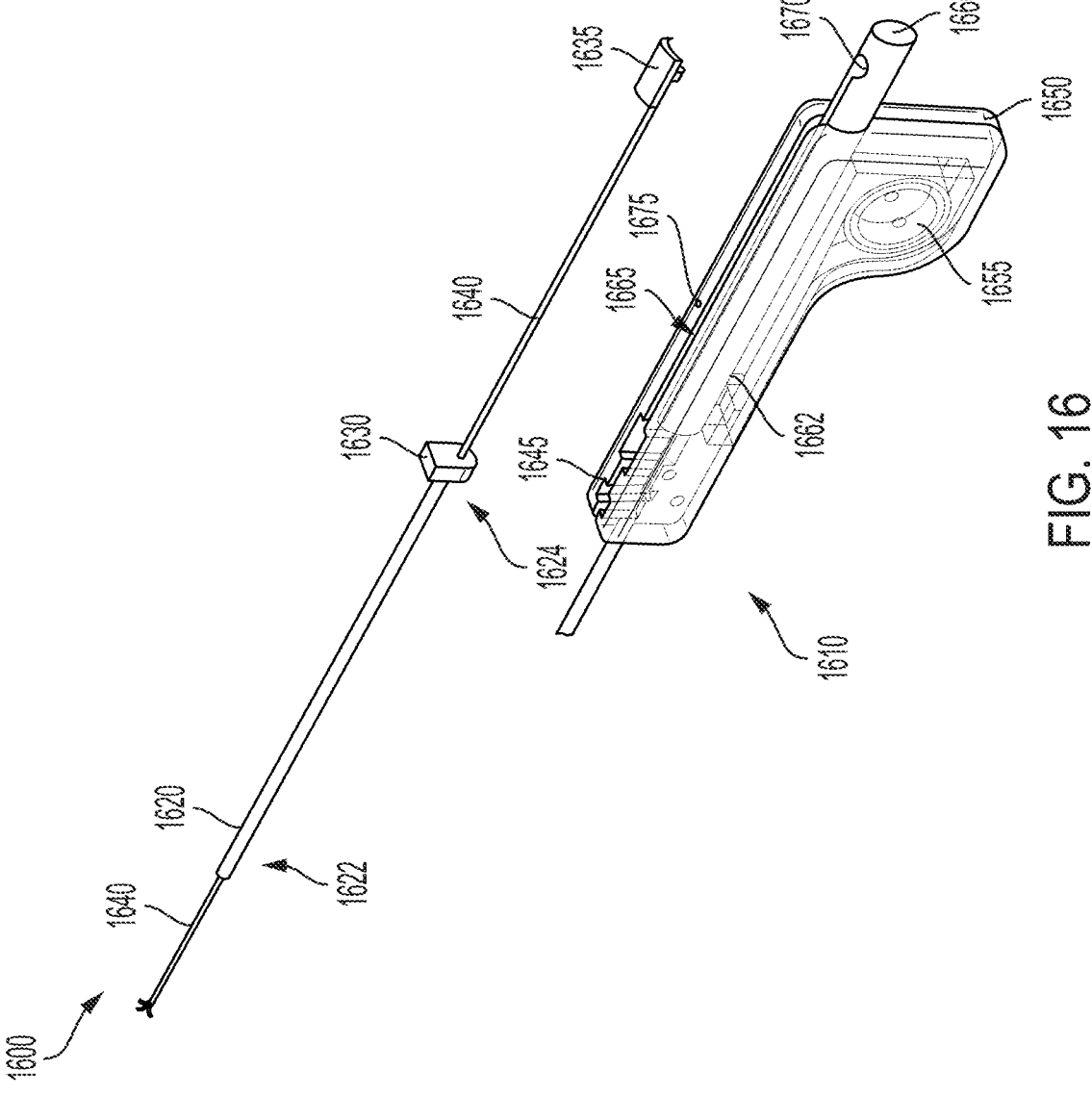
FIG. 16 is perspective partial exploded view of an alternative arrangement of an example dynamic vascular access and closure device in a first position.
Figure 17:
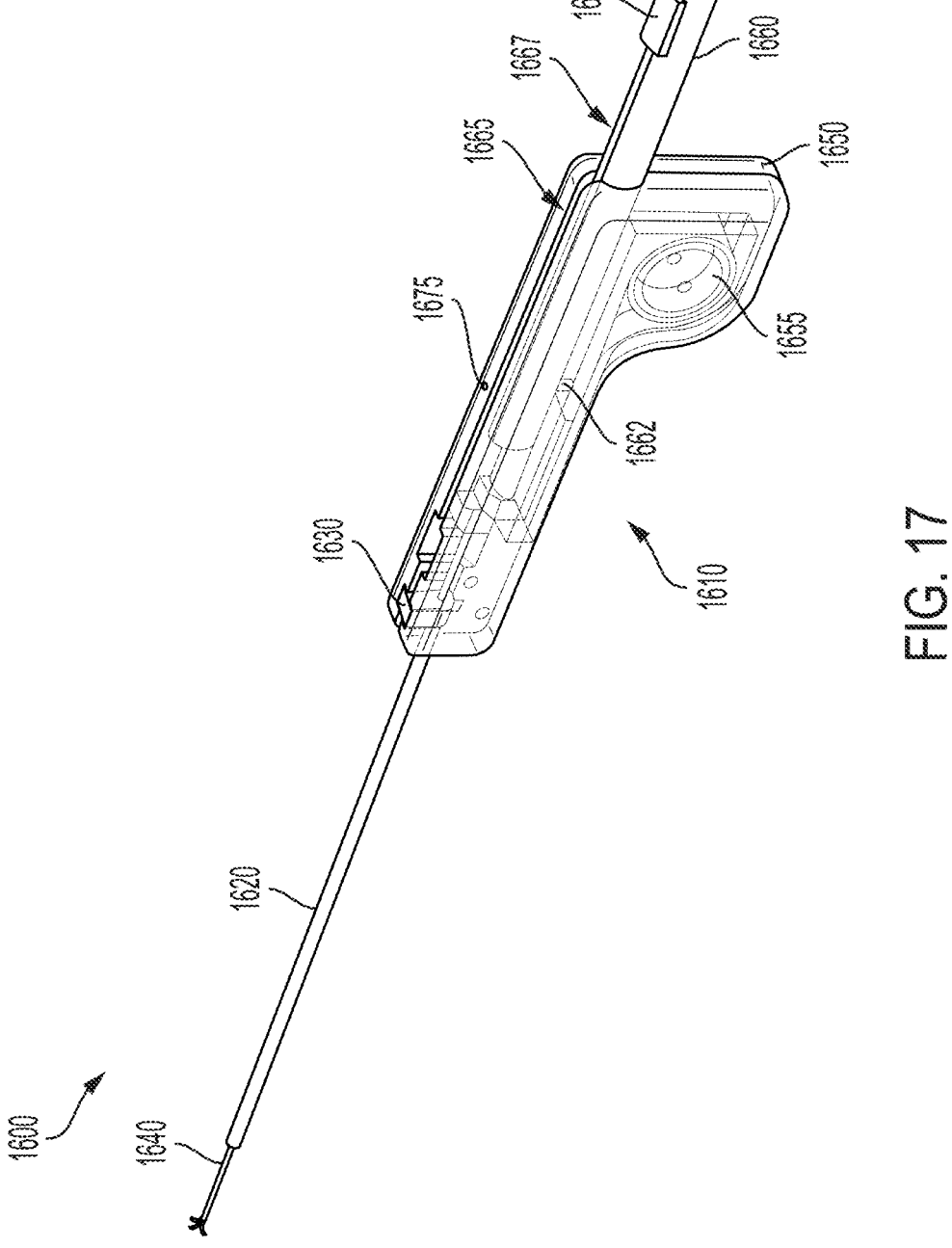
FIG. 17 is perspective view of an alternative arrangement of an example dynamic vascular access and closure device of FIG. 16 in a second position.

FIG. 16 is perspective partial exploded view of an alternative arrangement of an example dynamic vascular access and closure device 1600 in a first position. FIG. 17 is perspective view of an alternative arrangement of an example dynamic vascular access and closure device 1600 in a second position. As shown in the FIGS. 16 and 17, the dynamic vascular access and closure device 1600 includes a tensioning tube 1620 having a distal end 1622 and a proximal end 1624. The distal end 1622 is the working end that is placed in proximity to a blood vessel. One or more suture filaments 1640A-D (also, interchangeably referred to as suture wires and sutures) extend axially through the tensioning tube 1620 from the distal end 1622 through the proximal end 1624, where a distal end of each suture wire is coupled to a suture anchor (not pictured).

The proximal end 1624 of tensioning tube 1620 includes a protrusion 1630. Protrusion 1630 can take a variety of shapes and sizes. For example, as pictured, protrusion 1630 can be a hub with three flat sides and one rounded side. In other embodiments, protrusion 1630 could be a round hub with a circular cross section. In even further embodiments, protrusion 1630 could be a pin or protrusion that does not extend around the entire surface of tensioning tube 1620. Each of the plurality of sutures 1640 extends axially through the body of the tensioning tube 1620 and can be connected to a suture anchor 1635. The suture anchor is configured to attach each of the plurality of sutures to the rod 1660 of the spring assembly, as described in greater detail below.

Dynamic vascular access and closure device 1600 further includes a spring assembly 1610. Spring assembly can have a body 1650 that can be a housing for other components, such as spring 1655. Body 1650 can include a channel 1645 at its distal end being configured (i.e., sized and shaped) to receive protrusion 1630 of tensioning tube 1620. Body 1650 can further include an longitudinal slot 1665. The longitudinal slot can be open on the top surface of the body such that a proximal portion of the tensioning tube and proximal portion of each of the sutures can be placed into the body through the slot. The axial slot can also expose a longitudinal channel. The longitudinal channel can be configured to receive a elongated rod 1660. Rod 1660 can be disposed at least partially within the body 1650 and connected to the spring 1655. As illustrated in the FIGs. spring 1655 can be a constant force spring. Other spring types are also possible, for example, a coiled extension spring or compression spring. In some embodiments, spring 1655 may be a motor. Rod 1160 can further include a pin 1662. Pin 1662 can be connected to the spring 1655, for example through a hole in the spring or other suitable connection. Rod 1660 can further include a recess 1670 configured to engage suture anchor 1635. Suture anchor 1635 can include a protrusion configured to be received by recess 1670.

When a user wishes to connect the sutures and tensioning tube to spring assembly 1610 (i.e., after the sutures have been anchored in a vessel and tensioning of the sutures is desired), the protrusion 1630 of tensioning tube can be pressed into channel 1645 of body 1650 of the spring assembly 1610. Proximal ends of sutures 1640 can be placed into spring assembly 1610 through slot 1665 and connected to rod 1660 by engaging suture anchor 1635 with recess 1670 of rod 1660. Accordingly, a proximal end of each of the plurality of sutures 1640 can extend through the longitudinal slot 1665 of the body 1650 of the spring assembly 1610 and connect to the rod 1660. Consequently, a proximal portion of the rod 1660 can extend out of the body 1650 such that suture anchor 1635 does not interfere with body 1650. This proximal extension of rod 1660 also provides a surface for a user to pull or push on to move rod 1660 relative to body 1650 to tension or loosen sutures 1640. The distal portion of rod 1660 can stay within body 1650 and ride in its corresponding longitudinal channel. Body 1660 can also include a longitudinal channel in which sutures 1640 can be received to protect the sutures 1640 and prevent them from pinching or being cut while being tensioned or loosened.

Spring assembly 1610 can further include a spring or tension release 1675. The tension lock 1675 can include at least one of a button, a sliding switch, or a pin. For example, tension lock 1675 can include a hole in body 1650 and a corresponding hole or recess in rod 1660. A pin can be received in both the body hole and rod recess to lock the body 1650 and rod 1660 in place relative to one another. In other embodiments, a button or a sliding switch can be implemented to lock rod 1660 relative to body 1650. The tension lock 1675 can be positioned such that when the tension lock 1675 is engaged, there is slack in the sutures. When tension release 1675 is released, spring 1655 can pull on rod 1660 and cause it to move in a proximal direction, thus causing the same movement in sutures 1640, and creating tension in the sutures. Should the user wish to loosen the sutures, the user can push the proximal end of rod 1660 in the distal direction (toward the access site). Once rod 1660 is fully depressed (e.g., as illustrated by the position of rod 1660 in FIG. 16), the user could then reengage tension lock 1675 to lock rod 1660 in place and keep slack in the suture 1640. When the user is ready to tension the suture 1640 again, the user can disengage tension lock 1675 and the rod 1660 will return to its extended position (as illustrated by FIG. 17).

Body 1650, rod 1660, and suture anchor 1635 can be made from suitable metal or plastic materials. As described above, tensioning tube 1020 may be made from a variety of materials, such as polymers (e.g., plastics, rubber, etc.), metals or alloys (e.g., titanium, stainless steel), or any other suitable material with sufficient stiffness to prevent deformation under the compressive load applied by the tensioned sutures 1040A-D.

Figure 18:
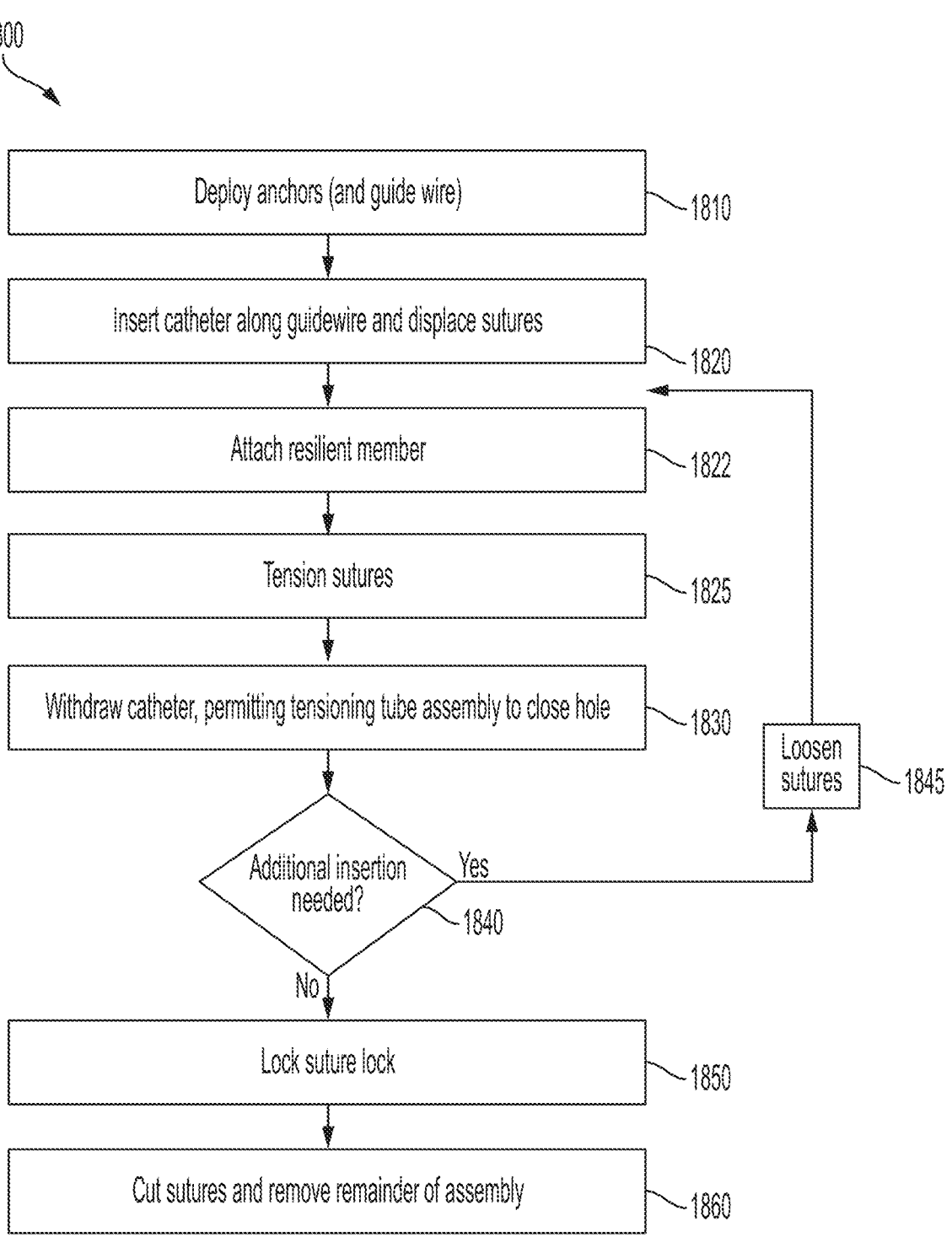
FIG. 18 is a flowchart illustrating another example method of using a dynamic vascular access and closure device.

FIG. 18 is a flowchart depicting an example method 1800 for using a dynamic vascular access and closure device 1600 of this disclosure. At step 1810, the anchors and/or sutures may be deployed into the vessel wall using any now or hereafter known deployment devices. Step 1810 may also include deploying of a guide wire. At this step, the dynamic vascular access and closure device can tension the sutures around the guidewire and/or an access site or hole in the vessel.

At step 1820, method 1800 may include inserting an interventional device over the guide wire into the vessel. In other embodiments, the sutures and tensioning device could be deployed before a vascular access. Accordingly, the anchors may be placed without a guidewire and the guidewire can be inserted after the placement of the device. As described herein, when the interventional device is inserted, the suture may be displaced or pulled, permitting the access site in the vessel to expand.

At step 1822, method 1800 may include attaching the resilient member. For example, step 1822 can include placing the tensioning tube and sutures into a spring assembly (e.g, spring assembly 1610 as described above).

At step 1825, method 1800 may include tensioning the sutures, for example by releasing a tension lock as described above with respect to dynamic vascular access and closure device 1600. The force applied to the sutures by the interventional device can cause a compression (or, in applicable embodiments, extension) of the resilient member within tensioning tube. The force applied by the resilient member to the sutures will hold the anchors close to the instrument, sealing the vessel wall around the periphery of the instrument and preventing or reducing any unwanted bleeding.

At step 1830, the interventional device may be withdrawn from the vessel. As the instrument is withdrawn, the access hole will be closed by the sutures automatically as the resilient member is decompressed, which in turn can push on the suture stops and cause the sutures to cinch together. This automated closure of the access site can prevent bleeding when the interventional device is removed from the vessel. Such automated bleeding prevention is a significant improvement over the existing techniques because a user is not required to manually pinch the vessel to prevent the bleeding. Other times, a physician may need to employ a cross-over balloon, which can be balloon inserted from another access site and inflated temporarily to stop bleeding. The automated cinching provided by disclosed embodiments may mitigate the need for such a technique. Accordingly, through use of the dynamic vascular access and closure device, the procedure is made both easier for the surgeon and safer for the patient.

As described herein, the dynamic vascular access and closure device 1600 of the disclosure also allows for reinsertion of an interventional device through the same access site. Accordingly, method 1800 may include a determination at step 1840 of whether an additional interventional device insertion is needed. If an additional interventional device insertion is needed, method 1800 may include step 1845 of loosening the sutures (for example, to prevent cutting or breaking of the sutures when the additional device is inserted). Loosening the sutures at step 1845 can include providing slack to the sutures by manually compressing rod 1660 distally, and optionally replacing or lock the tension lock. After loosening the sutures, step 1820 may be repeated. If an addition interventional device insertion is not needed, step 1850 may be executed. At step 1850, the suture lock can be locked. As described herein, the suture lock may be locked by crimping a ferrule or locking a selectable lock, among other ways. At step 1860, the sutures may be cut. The sutures maybe cut at any desired position, such as the distal end of the tensioning tube between the tensioning tube and the suture lock, leaving a relative minimum amount of extra suture attached to the patient's vessel. The tensioning tube assembly may be removed thereafter. In other embodiments, the suture could be cut at the proximal end of the resilient member, between the resilient member and the suture stop leaving a longer length of extra suture protruding from the suture lock (which may be used to tie a knot at the end of the suture lock to provide additional safety against unraveling of the sutures).

Figure 19B:
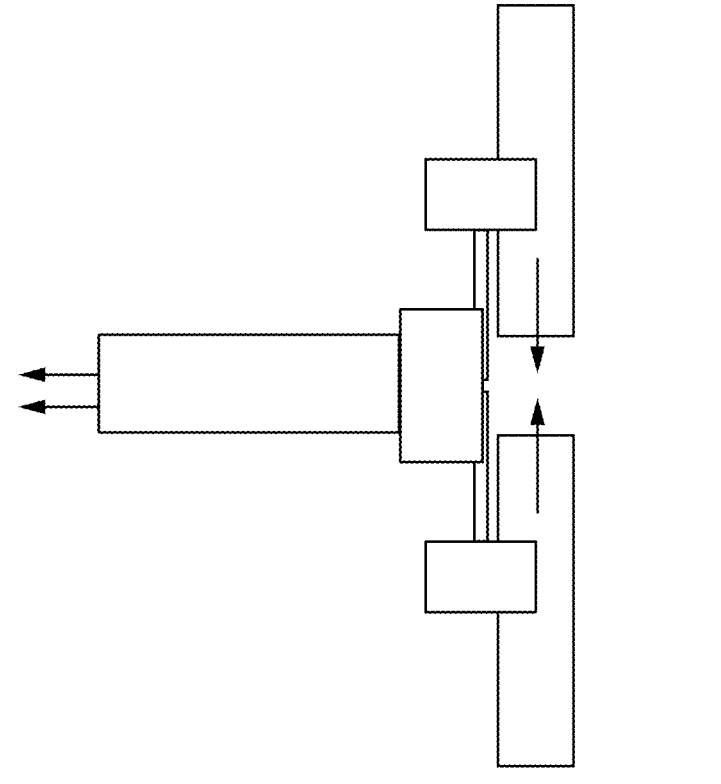
FIG. 19B is an illustration of a side view of an example dynamic vascular access and closure device with tensioned sutures showing force directions.
Figure 19A:
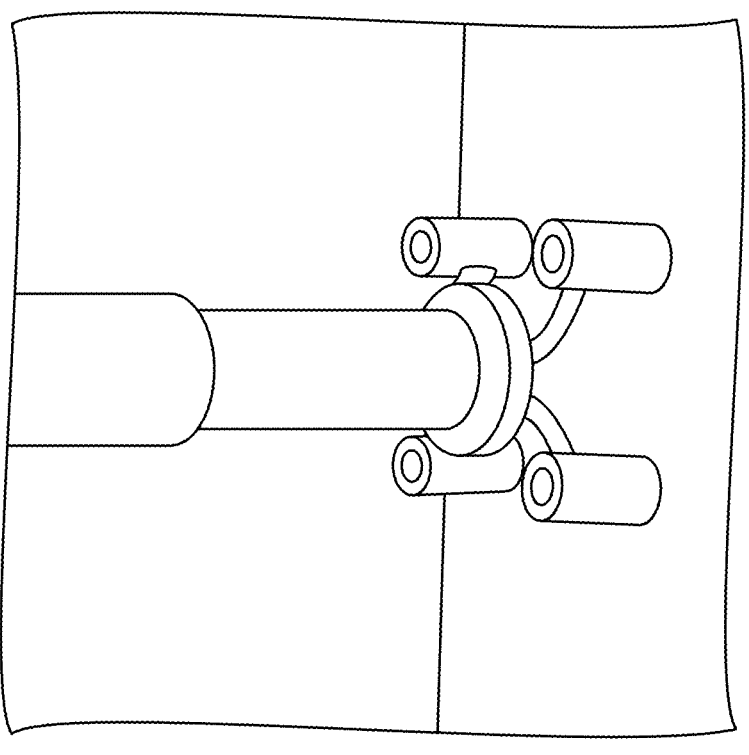
FIG. 19A is an illustration of a perspective view of a distal end of an example dynamic vascular access and closure device with tensioned sutures.

The disclosed devices and methods can be used to close vascular access sites using sutures with radial cinching (described below with respect to FIGS. 19A and 19B). In some examples, sutures are anchored by deployment of suture anchors at two or more locations about the periphery of an opening in an access site. After being distally anchored, sutures extend through a tensioning tube such that proximal ends of the sutures can be maneuvered after exiting a proximal end of the tensioning tube. When the sutures are tensioned, they cause radially inward cinching of the peripheral tissue of the opening at the access site (illustrated by the inward pointing arrows of FIG. 19B) because the tensioning tube, which has a distal end positioned near the opening, causes the sutures to createradial forces while preventing outwards movement of the sutures, thereby closing the opening. In some examples, the tensioning tube is axially rigid (while being flexible for bending) to prevent collapsing or kinking of the tensioning tube in a direction perpendicular to the longitudinal axis of the tube. As discussed above, the tensioning tube when positioned against (or near) the opening cause the sutures to pull the anchored sutures and tissue in towards the opening (instead of pulling of the tissue outwards towards the proximal end of the suture) to cause radial cinching of the opening. These radial cinching forces are illustrated by the horizontal arrows pointing towards each other in FIG. 19B. The tensioning tube converts the axial forces in the sutures (illustrated by the vertical arrows in FIG. 19B into these radial cinching forces. Optionally, another structure such as a suture lock may similarly aid in radial cinching of the access site when a distal end of the structure is positioned at or near the access site (with or without the tensioning tube).

Each of the plurality of sutures may be individually deployed, tensioned, advanced and/or otherwise controlled to selectively cinch an opening located between the suture anchors. For example, when four sutures are anchored in an approximate square shape around the periphery of an opening, application of similar tension on each of the four sutures will cause radial cinching of the opening symmetrically (i.e., approximately towards the center of the opening). On the other hand, variable tensioning of the sutures with respect to each other may cause asymmetrical radial cinching of the opening (i.e., offset with respect to the center of the opening). In various embodiments (for example, as illustrated by FIG. 19A), the arrangement of suture (once deployed around a vascular opening) may be configured to enable radial cinching by pulling the sutures (example, via suture anchors) towards a center of the suture arrangement where the vascular opening is located. For example, the suture may be deployed into tissue and/or structures around the opening such that when the sutures are tensioned the sutures radially cinch the opening inwards by pulling on the tissue and/or structures. Similarly, the sutures may be deployed in a manner that they form approximate vertices of a square, triangle, pentagon, hexagon, or the like with the opening being between the arrangement (center or off center). Additionally, sutures may be deployed asymmetrically about a vascular access site or opening depending on the size and shape of the access site or opening. Other arrangements are within the scope of this disclosure such as to allow for linear cinching, or the like.

It will be understood that terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements clearly indicate otherwise. For example, items described as "substantially the same," "substantially equal," or "substantially planar," may be exactly the same, equal, or planar, or may be the same, equal, or planar within acceptable variations that may occur, for example, due to manufacturing processes and/or tolerances. The term "substantially" may be used to encompass this meaning, especially when such variations do not materially alter functionality.

It will be understood that various modifications may be made to the embodiments disclosed herein. Likewise, the above disclosed methods may be performed according to an alternate sequence. Therefore, the above description should not be construed as limiting, but merely as exemplification of the various embodiments. Those skilled in the art will envision other modifications within the scope and spirit of the claims appended hereto.

What is claimed is:

1. A dynamic vascular access and closure device for radial cinching comprising:
a tensioning tube comprising a resilient member disposed within the tensioning tube;
a plurality of sutures extending axially between a distal end of the tensioning tube and a proximal end of the tensioning tube, wherein a proximal end of each of the plurality of sutures is configured to directly couple with the resilient member such that movement of the plurality of sutures causes compression or extension of the resilient member within the tensioning tube, and
a tension lock having a first position and a second position;
wherein:
in the first position, the tension lock is configured to hold the resilient member in a compressed state, causing slack in the sutures; and
in the second position, the tension lock is configured to permit extensions of the resilient member, causing tension in the sutures;
wherein the resilient member is configured to transition between:
a first position to cause the plurality of sutures to cinch a vascular access site situated between distal ends of the plurality of sutures when the distal ends of the plurality of sutures are attached to a blood vessel; and
a second position when the distal ends of the plurality of sutures are pulled apart to open the vascular access site, wherein a first length of the resilient member in the first position is greater than a second length of the resilient member in the second position.

2. The dynamic vascular access and closure device of claim 1, wherein the distal end of each of the plurality of sutures is coupled to a vascular anchor and the proximal end of each of the plurality of sutures comprises a suture stop.

3. The dynamic vascular access and closure device of claim 2, further comprising:
a suture lock; and
wherein the plurality of sutures, the vascular anchors, and the suture lock comprise a body-absorbable material.

4. The dynamic vascular access and closure device of claim 2, wherein each of the vascular anchors comprises a nitinol anchor.

5. The dynamic vascular access and closure device of claim 1, wherein the tension lock is a trigger suture.

6. The dynamic vascular access and closure device of claim 1, wherein the tension lock is a frangible bridge.

7. The dynamic vascular access and closure device of claim 1, wherein the tensioning tube comprises a resilient member stop.

8. The dynamic vascular access and closure device of claim 7, further comprising a force applicator disposed at a proximal end of the resilient member, and wherein the compression or extension of the resilient member within the tensioning tube comprises, via the force applicator, compression or extension of the resilient member with respect to the resilient member stop.

9. The dynamic vascular access and closure device of claim 8, wherein:
the tensioning tube further comprises a slot;
the force applicator further comprises a pin;
in the first position, the pin engages a stop on the tensioning tube; and
in the second position, the force applicator is rotated such that the pin engages the slot.

10. The dynamic vascular access and closure device of claim 7, wherein the resilient member stop comprises a step defined by a change in an internal diameter of the tensioning tube.

\* \* \* \* \*